(12) United States Patent
Alexander et al.

(10) Patent No.: US 10,143,358 B2
(45) Date of Patent: Dec. 4, 2018

(54) SYSTEM AND METHOD FOR A MAGNETIC ENDOSCOPE

(71) Applicant: TREBLE INNOVATIONS, LLC, Springville, UT (US)

(72) Inventors: Ian J. Alexander, Boerne, TX (US); Brian D. Owens, Plano, TX (US)

(73) Assignee: TREBLE INNOVATIONS, LLC, Springville, UT (US)

( * ) Notice: Subject to any disclaimer, the term of this patent is extended or adjusted under 35 U.S.C. 154(b) by 0 days.

(21) Appl. No.: 13/760,908

(22) Filed: Feb. 6, 2013

(65) Prior Publication Data

US 2013/0204085 A1 Aug. 8, 2013

Related U.S. Application Data

(60) Provisional application No. 61/595,885, filed on Feb. 7, 2012.

(51) Int. Cl.
*A61B 1/00* (2006.01)
*A61B 1/06* (2006.01)
(Continued)

(52) U.S. Cl.
CPC .......... *A61B 1/00158* (2013.01); *A61B 1/041* (2013.01); *A61B 1/05* (2013.01);
(Continued)

(58) Field of Classification Search
CPC . A61B 1/041; A61B 1/00158; A61B 1/00183; A61B 2560/0431; A61B 18/203;
(Continued)

(56) References Cited

U.S. PATENT DOCUMENTS 4,545,369 A  10/1985 Sato
4,604,993 A * 8/1986 Moriwaki .......... A61H 23/0263
                                                    601/18
(Continued)

FOREIGN PATENT DOCUMENTS

JP     2005046273 A    2/2005
WO  WO 2011/013733 A1  3/2011

OTHER PUBLICATIONS

"CellScope Launches iPhone Device for Diagnosing Ear Infections", http://block.launch.co/blog/cellscope-launches-phone-device-for-diagnosing-ear-infectio.html [retrieved from the Internet on May 28, 2013], 5 pages.

(Continued)

*Primary Examiner* — Timothy J Neal
*Assistant Examiner* — Aaron B Fairchild
(74) *Attorney, Agent, or Firm* — Goodhue, Coleman & Owens, P.C.

(57) ABSTRACT

A magnetic endoscopic system including a wireless endoscope. The wireless endoscope includes one or more cameras and one or more lights for viewing internal portions of a body. The wireless endoscope further includes one or more magnets. The magnetic endoscopic system also includes a positioner externally positioned against the body for moving the wireless endoscope when positioned entirely or partially within the portions of the body. The positioner includes at least one magnet for attracting the one or more magnets and magnetically moving the wireless endoscope.

7 Claims, 9 Drawing Sheets

(51) Int. Cl.
*A61B 1/05* (2006.01)
*A61B 1/04* (2006.01)

(52) U.S. Cl.
CPC ....... *A61B 1/00032* (2013.01); *A61B 1/00052* (2013.01); *A61B 1/042* (2013.01); *A61B 1/0607* (2013.01)

(58) Field of Classification Search
CPC ........ A61H 9/005; A61H 7/003; A61H 7/005; A61N 5/01; A61N 5/06; A61N 5/0616; A61N 2005/0632
USPC ................ 600/103, 109, 117, 118, 160, 173
See application file for complete search history.

(56) References Cited

U.S. PATENT DOCUMENTS

| | | |
|---|---|---|
| 4,862,874 A | 9/1989 | Kellner |
| 4,879,991 A | 11/1989 | Ogiu |
| 5,025,778 A | 6/1991 | Silverstein et al. |
| 5,117,818 A | 6/1992 | Palfy |
| 5,257,617 A | 11/1993 | Takahashi |
| 5,318,008 A | 6/1994 | Bullard |
| 5,599,301 A | 2/1997 | Jacobs et al. |
| 5,601,594 A | 2/1997 | Best |
| 5,879,289 A | 3/1999 | Yarush et al. |
| 5,941,818 A | 8/1999 | Hori et al. |
| 5,951,461 A | 9/1999 | Nyo et al. |
| 6,086,528 A | 7/2000 | Adair |
| 6,091,453 A | 7/2000 | Coan et al. |
| 6,106,457 A | 8/2000 | Perkins et al. |
| 6,165,123 A | 12/2000 | Thompson |
| 6,402,687 B1 | 6/2002 | Ouchi |
| 6,405,729 B1 | 6/2002 | Thornton |
| 6,432,046 B1 | 8/2002 | Yarush et al. |
| 6,750,971 B2 | 6/2004 | Overbeck et al. |
| 7,559,892 B2 | 7/2009 | Adler et al. |
| 7,897,061 B2 | 3/2011 | Dysard et al. |
| 8,088,101 B2 | 1/2012 | Chang et al. |
| 2001/0041825 A1 | 11/2001 | Shibata et al. |
| 2002/0068851 A1 | 6/2002 | Gravenstein et al. |
| 2003/0040685 A1 | 2/2003 | Lewkowicz et al. |
| 2003/0130564 A1 | 7/2003 | Martone et al. |
| 2004/0024334 A1* | 2/2004 | Boncompte ........ A61H 23/0245 601/2 |
| 2004/0027459 A1 | 2/2004 | Segawa et al. |
| 2004/0092825 A1 | 5/2004 | Madar et al. |
| 2004/0133089 A1 | 7/2004 | Kilcoyne et al. |
| 2005/0049462 A1 | 3/2005 | Kanazawa |
| 2005/0075538 A1 | 4/2005 | Banik et al. |
| 2005/0171418 A1* | 8/2005 | Lin ............................ 600/109 |
| 2005/0177024 A1 | 8/2005 | MacKin |
| 2005/0228224 A1 | 10/2005 | Okada et al. |
| 2006/0137690 A1 | 6/2006 | Gunaratnam et al. |
| 2006/0161045 A1 | 7/2006 | Merril et al. |
| 2006/0183971 A1 | 8/2006 | Haviv |
| 2006/0206005 A1 | 9/2006 | Ou-Yang et al. |
| 2006/0235458 A1 | 10/2006 | Belson |
| 2006/0272640 A1 | 12/2006 | Abullon |
| 2007/0142703 A1* | 6/2007 | Lu .................................. 600/109 |
| 2007/0161853 A1 | 7/2007 | Yagi et al. |
| 2007/0162095 A1 | 7/2007 | Kimmel et al. |
| 2007/0185377 A1 | 8/2007 | Murakami et al. |
| 2007/0219600 A1 | 9/2007 | Gertner et al. |
| 2007/0276183 A1 | 11/2007 | Melder |
| 2008/0021273 A1 | 1/2008 | MacKin |
| 2008/0081947 A1* | 4/2008 | Irion ...................... A61B 1/041 600/173 |
| 2008/0103521 A1 | 5/2008 | Makower et al. |
| 2008/0139881 A1 | 6/2008 | Cover et al. |
| 2008/0139884 A1* | 6/2008 | Myers .......................... 600/118 |
| 2008/0232131 A1 | 9/2008 | Suda |
| 2008/0275483 A1 | 11/2008 | Makower et al. |
| 2008/0312499 A1* | 12/2008 | Handa et al. ................. 600/109 |
| 2009/0076330 A1 | 3/2009 | Ashida |
| 2009/0095303 A1 | 4/2009 | Sher et al. |
| 2009/0187071 A1 | 7/2009 | Kim |
| 2009/0188507 A1 | 7/2009 | LaCava |
| 2009/0194109 A1 | 8/2009 | Doshi et al. |
| 2009/0247828 A1 | 10/2009 | Watanabe et al. |
| 2009/0253967 A1 | 10/2009 | Gill et al. |
| 2010/0016673 A1 | 1/2010 | Bandy et al. |
| 2010/0030031 A1 | 2/2010 | Goldfarb et al. |
| 2010/0063358 A1 | 3/2010 | Kessler |
| 2010/0095969 A1 | 4/2010 | Schwartz et al. |
| 2010/0099946 A1 | 4/2010 | Jenkins et al. |
| 2010/0100181 A1 | 4/2010 | Makower et al. |
| 2010/0101580 A1 | 4/2010 | Stumm et al. |
| 2010/0210901 A1 | 8/2010 | Makower et al. |
| 2011/0137290 A1 | 6/2011 | Flickinger et al. |
| 2011/0261183 A1 | 10/2011 | Ma et al. |
| 2012/0071824 A1 | 3/2012 | Chang et al. |
| 2013/0204085 A1 | 8/2013 | Alexander et al. |

OTHER PUBLICATIONS

Aliexpress "Witson New Wifi iPad iPhone Android supported borescope, 9.8mm camera with 2 Leds, Support iPad/iPhone/Android surveilance", http://www.aliexpress.com/store/product/Witson-New-Wifi-iPad-iPhone-aNDROID-Supp... [retrieved from the Internet on May 2, 2013], 12 pages.

Euroclinic Medial Equipment, Diagnostic & Imaging. "EVS ED400 Camera System", http:www.euroclinic.it/en/product-php?p=78&d=3, retrieved from the Internet on May 2, 2013], 2 pages.

Sanostec, Inc., Sinus Cones vs. Max-Air Nose Cones, Retrieved Nov. 15, 2011 from http://www.maxaimosecones.com/sinus-cones-vs-max-air-nose-cones-products/.gclid=CLrys4--3wsCFYxb7AodiXezQA.

SweetVision Imaging, innovative endoscope imaging systems, http:sweetvision-imaging.com [retrieved from the Internet on May 2, 2013], 10 pages.

* cited by examiner

SYSTEM AND METHOD FOR A MAGNETIC ENDOSCOPE

RELATED APPLICATIONS

This application claims priority to U.S. provisional patent application Ser. No. 61/595,885 filed Feb. 7, 2012 the entire contents of which are all hereby incorporated by reference in their entirety. This application is related to U.S. utility patent application Ser. Nos. 13/303,117, 13/654,401, and 13/654,409 filed Nov. 22, 2011, Oct. 17, 2012, and Oct. 17, 2012, respectively, the entire contents of which are all hereby incorporated by reference in their entirety.

BACKGROUND

Each year more and more surgical procedures are performed through the body orifices or surgically created openings. Procedures and surgeries within the body of the patient require positioning the necessary equipment, such as endoscopes and laparoscopes. Endoscopy refers to looking inside and typically refers to looking inside the body for medical reasons using an endoscope, an instrument used to examine the interior portion of a body, such as a hollow organ or cavity of the body.

Some endoscopic procedures may require multiple medical professionals and imaging systems to ensure proper guidance and placement of the equipment due to the size, bulk, and awkwardness of the equipment. For example, many endoscopes may include handles, scopes, external processing equipment, and custom displays. The endoscopes may also be difficult to manipulate when inserted partially or completely in the patient's body. In many cases, the endoscopes may be extremely expensive preventing many medical professionals from purchasing or using endoscopes despite the many advantages offered. In many ways, current systems, devices, and techniques for performing endoscopic procedures fail to adequately address these and other issues.

SUMMARY

One provides an endoscopic system, a method of utilization, and a magnetic endoscope. A magnetic endoscopic system may include a wireless endoscope. The wireless endoscope may include one or more cameras and one or more lights for viewing internal portions of a body. The wireless endoscope may further include one or more magnets. The magnetic endoscopic system may also include a positioner externally positioned against the body for moving the wireless endoscope when positioned entirely or partially within the portions of the body. The positioner may include at least one magnet for attracting the one or more magnets and magnetically moving the wireless endoscope.

Another embodiment provides an endoscopic system. The endoscopic system may include a wired endoscope for partial insertion into a body. The wired endoscope may include one or more magnets for positioning a camera of the wired endoscope. The endoscopic system may further include a positioner for being positioned against a body of a patient including at least one magnet for magnetically interfacing with the one or more magnets of the wired endoscope to position the wired endoscope.

Another embodiment provides an endoscopic system. The endoscopic system may include a wireless endoscope configured to be inserted into a body of a patient. The wireless endoscope may include one or more magnets, a camera, and a light. The endoscopic system may also include a positioner externally positioned against the body for moving the wireless endoscope within the body of the patient. The positioner may include at least one magnet for attracting the one or more magnets and magnetically moving the wireless endoscope.

Another embodiment provides an endoscopic system. The endoscopic system may include an endoscope configured to be inserted into a body of a patient. The wireless endoscope includes one or more magnets, a sensor, and an energy source. The endoscopic system further includes a positioner externally positioned against the body. The positioner comprises at least one magnet for attracting the one or more magnets and magnetically moving the wireless endoscope within the body of the patient.

BRIEF DESCRIPTION OF THE DRAWINGS

Illustrative embodiments of the present invention are described in detail below with reference to the attached drawing figures, which are incorporated by reference herein and wherein.

DETAILED DESCRIPTION OF THE DRAWINGS

Figure 1:
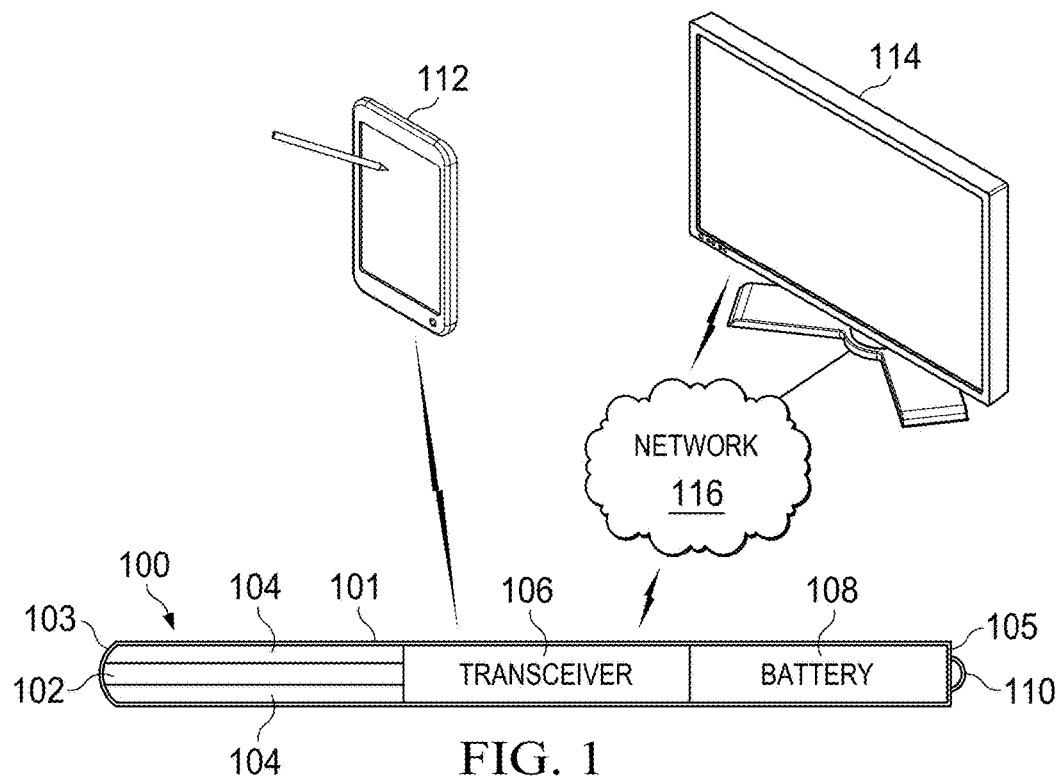
FIG. 1 is a schematic, pictorial representation of a wireless endoscope in accordance with an illustrative embodiment.

The illustrative embodiments provide a magnetic endoscope. The magnetic endoscope may be configured to be completely or partially inserted within the body of a patient. The magnetic endoscope may be utilized in a wireless or wired configuration. The magnetic endoscope may be configured to communicate directly or indirectly (e.g., through a network) with a computing or communications device. The computing device may be a personal computer, laptop, desktop computer, or other data processing system or device. The communications device may be a wireless device, such as a cell phone, electronic book, mp3 player, media system, gaming system, PDA, tablet, iPhone, iPad, appliance, or so forth. The magnetic endoscope may be utilized to capture information about its surroundings, such as for example, image content including but not limited to video, images, and content in any number of spectrums, wavelength, and so forth.

In an illustrative embodiment, the magnetic endoscope is small, portable, light weight, inexpensive, and able to be utilized with existing electronic devices used by or available to a medical professional. As a result, many patients that have not previously benefited from endoscopic analysis and treatment may receive the associated medical examination, analysis, and treatment. The magnetic endoscope may be controlled related to its surroundings by a positioner.

One or more magnets of the magnetic endoscope and positioner may be utilized to move, position, rotate, gyrate, angle, and reconfigure the camera or visualization components of the magnetic endoscope to capture video or still images needed by a medical professional. The magnets may include any circuitry, whether AC or DC powered, that uses or moves an electric charge or electrons to create a magnetic affect or field of influence. By way of example, magnets that produce a magnetic field may be utilized to attract other ferromagnetic materials and attract or repel other magnets. The magnets may include permanent magnets (e.g., ferromagnetic materials, rare earth magnets, natural magnets, etc.), electromagnets, injection molded magnets, flexible magnets, and so forth. The overall strength (including magnetic moment and total magnetic flux) of the magnets may be selected based on natural variation or may be controlled by user input or variation, whether electrical, mechanical, structural, or otherwise. Specific examples of magnets utilized in the described embodiments may include neodymium-iron-boron (NIB) magnets, ferrite magnets, Mn-alloy magnets, and so forth. The magnets may be integrated with or attached to the different devices, components, or systems.

The magnetic endoscope may also be physically connected to the positioner or other anchor component by a lanyard or tether. The lanyard prevents the inadvertent loss or inability to retrieve the magnetic endoscope. The lanyard may also include a communications component (e.g., twisted pair, traces, wires, busses, etc.) that may be utilized to communicate data, commands, or image content in a wired configuration.

In one embodiment, the magnetic endoscope is a plug-and-play device or wireless device equivalent that may be utilized without specialized software or other components. A plug-and-play device provides a standard for the connection of peripherals, such that the magnetic endoscope only needs to be connected to a computer or computing device in order to function as desired without additional requirements. For example, the default or installed software of the computing or communications device may be utilized to both view content, save content, and otherwise manage the content. The computing or communications device may not need specific drivers, software, or other applications. As a result, the user may utilize the magnetic endoscope with any number of commonly available electronic devices (e.g., wireless telephone, laptop, computer, mp3 player, e-reader, tablet, etc.) that have an electronic display and in any number of locations, configurations and circumstances.

In another embodiment, the magnetic endoscope may be utilized with specialized logic or software for capturing, saving, editing, flagging, notating, and sharing the content with any number of other users, such as doctors, nurses, dentists, physicians assistants, coworkers, or so forth. The logic or software may be included in an operating system, kernel, program, set of instructions, or mobile application. For example, the image content, video, images or other captured content by the magnetic endoscope may be communicated, transferred, or shared with a medical professional, system, or networked device(s) based on a request from the medical professional. The communications may occur in response to an association of the device with an identifier of the magnetic endoscope, or in response to a request from the user. For example, a MAC address, IP address, website, dedicated server, IMEI, or other identifier may be utilized to send and receive content captured by the magnetic endoscope.

The magnetic endoscope may be utilized for any number of medical examinations including examining laparoscopic examinations of the abdomen and internal organs. The magnetic endoscope may be inserted through natural or surgically created openings in the body (e.g., laparoscope through a patient's belly button). The magnetic endoscope may also be utilized for analysis, structural review, or in any other number of circumstances where a small camera may be required. For example, during some laparoscopic procedures a second camera positioned against the abdominal wall may be very useful.

In one embodiment, the magnetic endoscope may be disposable for one time or field use. In another embodiment, the endoscopic peripheral may be configured for cleaning, sanitizing, or may include a disposable cover for utilization with a number of patients or uses.

Another embodiment provides a wireless endoscope. In one embodiment, the wireless endoscope is a wand-shaped endoscope that may be utilized alone or with a guiding device, such as a surgical guide or nasal guide. The wireless endoscope has a reduced footprint and is self-contained to wirelessly transmit video or still-images ("images" or "content") to one or more displays, which may be wired or wireless devices.

In another embodiment, the camera of the wireless endoscope may communicate and be powered through a wire or cable with an externally-connected transmitter and battery, or powered wirelessly, for example, by electromagnetic induction generated by a positioner or other device. The wireless endoscope decreases the size and complexity of endoscopic systems and equipment. In addition, the wireless endoscope may include interchangeable parts including a camera, lights, processing or logic components, a transmitter or transceiver, and/or a battery that may be adapted for the patient, medical professional, or medical procedure. The magnetic endoscope and wireless endoscope may be utilized for any sort of visualization, approximation or interpretation within the body of a patient. The wireless endoscope may be utilized in a wireless mode or wired mode (when physically connected to and powered by or charged by a computing or communications device). Unless otherwise indicated, as used herein, "or" does not require mutual exclusivity.

Any of the components and features of the illustrative embodiments, including the priority applications and related applications, may be combined in a nearly unlimited number of configurations best suited to fit the body of the patient and/or the needs of medical professionals.

In the illustrative embodiments, the term "patient" is utilized to refer to any individual, user, animal, or living creature that may have a medical procedure or other process performed through a natural opening or orifice of the body or surgically created opening of the body.

The wired or wireless endoscope may be utilized alone or with other medical instruments through naturally or surgically-created openings, including, but not limited to, laparoscopic, abdominal, pelvic, chest, head, neck, intracranial, ear, extremity, cardiac or vascular procedures or diagnostic evaluations.

Figure 2:
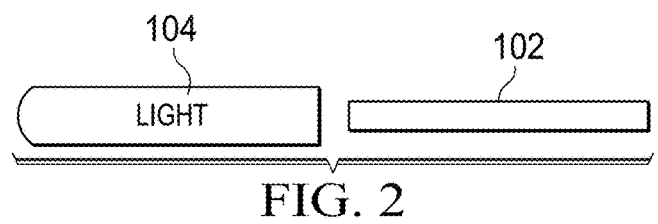
FIG. 2 is a schematic, side view of a cylindrical light and camera in accordance with an illustrative embodiment.
Figure 5:
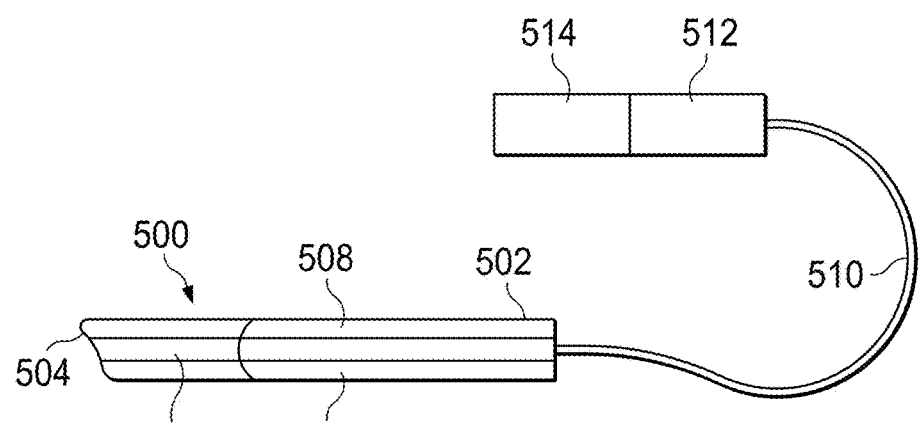
FIG. 5 is a schematic, pictorial representation of the wireless endoscope in accordance with an illustrative embodiment.

Turning now to FIGS. 1, 2 and 5, schematic, pictorial representations of a wireless endoscope 100 are provided in accordance with illustrative embodiments. An endoscope is an instrument that may be introduced into the body of an individual or patient to acquire information such as by providing images of its surroundings or to give a view of internal parts. The wireless endoscope 100 may be utilized in very small spaces and is easier to use than existing endoscopes. Existing endoscopes are generally bulky and not ergonomically shaped and may require two or more medical professionals to operate effectively (e.g., a doctor and nurse). In one embodiment, the wireless endoscope 100 is a wireless scope that is compacted or configured into a reduced footprint or size. The wireless endoscope 100 may be utilized by a single user or positioned a single time or as needed within the body of the user to free up the hands of the medical professional. The wireless endoscope 100 may include magnetic components, electro-magnetic components or other features or components that allow an external control or influence to act upon it, such as a metal case or magnets for positioning, securing, and moving one or more portions of the wireless endoscope 100.

The wireless endoscope 100 may be sanitized for repeated use or may be a disposable one-time use wireless endoscope 100. The wireless endoscope 100 may be a wand or cylindrical-shape for easy handling by a medical professional. In other embodiments, the wireless endoscope 100 may be spherically-shaped, an ovoid, or so forth. In one embodiment, the wireless endoscope 100 has a diameter or cross-sectional measurement of between 1 mm to 10 mm, although the diameter may vary widely depending on the particular application or embodiment. In addition, the diameter of the different sections of the wireless endoscope 100 may vary. For example, a front portion may include a section including a fiber optic light and camera with a diameter of approximately 1 mm that is attached to a section with a greater diameter of 10 mm for the transceiver 106 and battery 108.

The wireless endoscope 100 may be a stand-alone device or may be utilized or integrated with other medical devices. For example, the wireless endoscope 100 may be built into one or more of the lumens of a surgical instrument.

Figure 3:
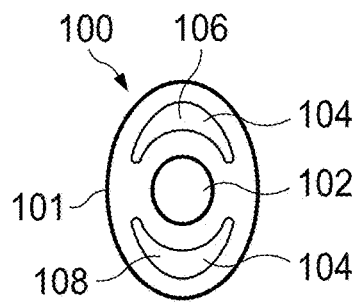
FIGS. 3 and 4 are schematic, front views of the wireless endoscope in accordance with illustrative embodiments.
Figure 4:
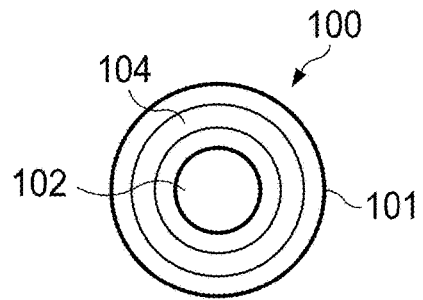

As shown in the schematic front views of FIGS. 3 and 4, the wireless endoscope 100 may be shaped as a circle, oval, ellipse, or a rounded triangle shape. The wireless endoscope 100 may be utilized for any number of medical or non-medical procedures or examinations that are known in the art. In one embodiment, the wireless endoscope 100 is configured to be received by an opening, lumen, or port of a medical instrument or tool. The wireless endoscope 100 may be utilized as a stand-alone device that is inserted to a required depth and positioned to display a video image of its surroundings to the medical professional. The wireless endoscope 100 may be moved and positioned utilizing one or more magnets, such as magnet ends of different polarity, a metallic case, or so forth.

In another embodiment, friction, tight tolerances, or interference fittings of the opening and external dimensions of the wireless endoscope 100 may be utilized to secure the wireless endoscope 100. In an alternative embodiment, the wireless endoscope 100 may include a positioning motor for moving the wireless endoscope 100 or camera 102 in and out, rotating the wireless endoscope 100, or otherwise positioning the wireless endoscope 100 within the examined space. The same may be performed for a camera 102 without necessarily requiring movement of the other components/features of the wireless endoscope.

In one embodiment, the wireless endoscope 100 may include the camera 102, a light 104, a transceiver 106, a battery 108, and a magnet 110. The electrical components of the wireless endoscope 100 may be enclosed in a case 101. In one embodiment, the case 101 is a waterproof housing or framework completely sealing in (e.g., forming an enclosure around) and securing the components of the wireless endoscope 100. The case 101 may include any number of seals and watertight connections ensuring that the wireless endoscope 100 may be utilized multiple times without damage from fluids. For example, the case 101 may be formed entirely of a metal, polymer, plastic, or glass. In another embodiment, different components and materials may be fused together or interconnected to form an enclosure. For example, the main body of the case 101 may be formed of stainless steel with a glass end or lens (not shown) for the light 104 to shine through and the camera 102 to retrieve video images. For example, the case 101 may be formed of two different halves that are screwed together utilizing threads or otherwise attached utilizing tabs, an interference fit, o-ring seal or so forth for utilization.

In one illustrative embodiment, the case 101 is formed from hypoallergenic medical grade materials, such as U.S. Pharmacopeia (USP) Class V and VI silicon, rubber, polymers, or plastic materials (or a combination thereof), including those known in the art. All or portions of the wireless endoscope 100 and described magnetic endoscopes may be clear or transparent to provide the medical professional with maximum visibility of the body. In one example, the case 101 or respective components may be machined or otherwise manufactured from a single piece of medical grade metal, magnet or molded from plastic, silicon, composite, or rubber. Alternatively, multiple components of different materials may be interconnected or fused together. In one embodiment, a portion of the case 101 is formed of plastic that is see-through, translucent, or transparent to provide the medical professional additional visibility. All or portions of the case 101 may also act as a lens for bringing into focus light emitted by the light 104 and images received by the camera 102. As a result, a light source may illuminate areas around the wireless endoscope 100.

The case 101 or exterior or external portions of the wireless endoscope 100 (including a case, cover, tether, or cable) may also have anti-fungal, anticoagulant, procoagulant, and/or anti-bacterial properties for preventing the spread of infections when used. For example, the material of the case 101 may be formulated, molded, impregnated, injected, coated, or otherwise created with any of the described compounds, materials, or properties to prevent any unwanted spread of germs or infection. For example, the wireless endoscope 100 or an interior portion of the wireless endoscope 100 inserted into the nose may be coated with or excrete an anesthetic agent, such as lidocaine creme to make insertion and operation of the wireless endoscope 100 more comfortable.

In one embodiment, the wireless endoscope 100 may be used a single time before being disposed. The wireless endoscope may also be configured for repeated use, including repeated use after sterilization. For example, the case 101 may be run through and sanitized by an autoclave without being ruined or altered. The electrical components may also be placed or positioned within a new or sterilized case 101 for utilization.

In one embodiment, the case 101 includes the contacts, interfaces, wires, or busses for each of the internal electrical components. For example, the camera 102 and/or light 104 may contact a video bus integrated within the frame for transmitting the video signal to the transceiver 106 for transmission. The light 104 may also include an interface for communicating video signals from the camera 104 to the case 101 or directly to the transceiver 106. In one embodiment, the bus for sending and receiving video or commands may be insulated or the case 101 may include a designated space ensuring that none of the components contact the bus. Likewise, a wire or power conduit integrated within the case 101 may communicate an electrical signal from the battery 108 to the transceiver 106, light 104, and/or camera 102. Alternatively, the electrical components may be serially connected in the positioned order for both powering the components and communicating a video signal (and command signals as needed).

A first end 103 of the case 101 may include or be formed of a lens or transparent plastic cover focusing or allowing light to be acquired as video content by the camera 102. Any number of lenses may be utilized depending on the medical procedure being performed. For example, the lens may be a simple convex, biconvex, plano-convex, positive meniscus, negative meniscus, plano-concave, macro, zoom, apochromat, process, fisheye, stereoscopic, infrared, ultraviolet, swivel, biconcave, or other optically configured lens. The lens may also be selected to prevent fluids from accumulating on the camera 102 and light 104 blocking the view of the relevant site. The lens may be impregnated or coated with or excrete a hydrophobic agent to aid in keeping fluid or other matter from accumulating on the lens.

In one embodiment, the camera 102 is a condensed digital video camera configured for wirelessly communicating the video content through the transceiver 106. The camera 102 may be configured to capture video in response to the output of the light 104, which may broadcast visible light, specific spectrums, infrared, ultrasound, ultra violet, x-ray, gamma ray, positron emission tomography (PET), single-photon emission tomography (SPECT), magnetic resonance imaging, spectroscopy, and elastography or other electromagnetic or non-electromagnetic imaging, energy or signals (e.g. EKG, EEG, EMG, PPG, EIT, ENoG, ERG, ENG, MEG, VEP, etc.). In one embodiment, the light 104 may be a fiber optic light that is powered by external sources. In another embodiment, the light 104 may be an energy source configured to emit one or more of the aforementioned outputs.

Any kind of digital, analog, or fiber optic imaging or viewing device may be used. In one embodiment, the camera 102 is a charge coupled device (CCD) camera, such as a CMOS camera composed of multiple stacked and interconnected semiconductor layers. The camera 102 may be configured or selected to correspond to, pick-up, or capture the type of light 104 inserted or installed in the wireless endoscope 100. The camera 102 may be manually or remotely controllable. For example, the camera 102 may include a swivel lens that rotates to give unique perspectives and camera angles. The lens or camera 102 may be configured to protrude from or extend from the wireless endoscope 100. In another embodiment, the camera 102 may be a fiber optic camera. In still another embodiment, the camera 102 may be a collector configured to acquire a response from an output emitted by an energy source as discussed above.

In another embodiment, the diameter of the wireless endoscope 100 may narrow substantially between portions of the wireless endoscope 100 to provide flexibility as well as potential movement of the camera 102 and the light 104 for enhanced visualization. For example, the portion of the wireless endoscope 100 including the camera 102 and the light 104 may narrow to provide a fiber optic camera and light that may be directionally controlled utilizing actuators, magnetics, pneumatics, wires, piezo components, or microelectromechanical systems (MEMS). The movement of the light 104 and/or camera 102 may be correlated so that movement of one tracks with movement of the other.

The camera 102 may utilize any number of electronic or even vibrational spectra for chemical analysis, oximetry, disease classification, and molecular microscopy. For example, the camera 102 may also be configured to include features of a microscope. In addition, diffuse reflection, fluorescence reflectance (fluorescence spectroscopy), Raman reflectance (Raman spectroscopy), and absorption may be observed, measured, or recorded by the camera 102. The available or desired wavelength or spectrum may affect the light 104 and camera 102 selected for the wireless endoscope 100. The camera 102 may be configured to produce 1-D spatial information utilizing a single wavelength or spectrum, 2-D spatial information utilizing widefield spectroscopy/hyperspectral imaging, and 3-D spatial information utilizing tomography. The camera 102 may be selected for a particular light 104 or based on characteristics of the camera 102 or generated video signal including resolution, intensity, frame rate, signal-to-noise ratio (SNR), peak SNR, noise immunity, timing, scanning, and so forth. In another embodiment, the camera 102 may be a collector such as a sensor for acquiring and measuring reflectance or absorption of the above described energy source.

The image content or video captured by the video camera may be transmitted directly or indirectly to the wireless device 112 or computing device 114. For example, the wireless endoscope 100 may communicate with the computing device 114 through a network 116. The network 116 may utilize a communication standard, such as 802.11 (e.g., 802.11n) as the standard continues to be updated. The direct or indirect communications may represent Bluetooth, ZigBee, WiFi, wireless local area network (WLAN), WiMAX, proprietary standards, or other radio frequency signals whether analog or digital that may be utilized to communicate a video signal. Any number of FCC, FDA, IEEE, ISO, CEN, ETSI, ARIB, ANSI, or IEC approved communications protocols or standards may also be transmitted by the transceiver 106. Indeed, the types of wireless or wired standards or methods of communication are numerous.

The video or image signal may be received and displayed by the wireless device 112 and/or computing device 114 in real-time. The video signal may be formatted before or after being sent from the wireless endoscope 100. In one embodiment, the wireless endoscope 100 may include a processor, ASIC, FPGA, graphics card or chip, and/or other logic for managing the wireless endoscope 100 and processing the video signals. The video may be compressed in a raw or formatted state for communication by the transceiver 106. For example, the video content may be packetized and communicated with or without encryption. Error detection and known packet analysis, processing, decryption, and other similar steps may be performed by a receiving device. In one embodiment, the wireless endoscope 100 may include a memory for storing the video content for subsequent analysis, review, documentation, training, or educational purposes. Alternatively, the video may be recorded by the wireless device 112 or computing device 114 for the same reasons. The wireless device 112 and computing device 114 may also act as a server to deliver or save content to any number of other client devices, systems, equipment, streaming configurations, or databases.

In another embodiment, a cable or wire may be utilized to communicate the video directly to the wireless device 112, computing device 114, or to an external transceiver that is not integrated with the case 101 of the wireless endoscope. (see, e.g., FIG. 5 below). The same cable may also be utilized to transmit power to the wireless endoscope 100 from a remote location further reducing the required size of the wireless endoscope 100. For example, a USB cable (e.g., standard, mini, micro, etc.) connected to the wireless endoscope 100 and wireless device 112 may both power the wireless endoscope 100 and communicate video to the wireless device 112.

A second end 105 of the case 101 may be removable for inserting or removing the components of the wireless endoscope 100. For example, the second end 105 of the case 101 may snap in, interconnect, latch, or include threads for securing and one or more gaskets for sealing the components of the case 101. The wireless endoscope 100 may communicate with the wireless device 112 or the computing device 114.

In one embodiment, the components of the wireless endoscope 100 may be interchangeable. For example, even the relative positioning of components within the case 101, such as the transceiver 106 and battery 108, may be varied. For example, the transceiver 106 may more efficiently transmit and receive signals when positioned at the second end 105 of the wireless endoscope 100 where the battery 108 is shown. As a result, the wireless endoscope 100 may be configured for each patient or medical professional. For example, different cameras or batteries may be inserted into the case 101 for different situations. In one embodiment, the video camera 102 may be an infrared camera or spectrum-specific camera configured to view blood flow (or the lack thereof) within the nose. In another embodiment, the components of the wireless endoscope 100 are permanently connected. In another embodiment, the components are contained and sealed within case 101.

In one embodiment, the components of the wireless endoscope 100 are powered by an electrochemical cell, such as a battery 108. The battery 108 may be a high-powered energy storage device. For example, the battery 108 may be a rechargeable or one-time use polymer battery, alkaline, zinc-air battery, lithium ion battery, thin film battery, ultra-capacitor, fuel cell, piezo electric generator, or other capacitors or batteries being developed and known in the art. The wireless endoscope 100 may be utilized repeatedly by replacing or recharging the battery 108 as needed.

In another embodiment, the wireless endoscope 100 may include a port or inductive charger (not shown) for recharging the battery 108 without removing the battery 108 from the case 101. Similarly, the wireless endoscope 100 may be configured to function in a wireless or wired state. For example, the wireless endoscope 100 may be connected directly to the computing device 114 utilizing a cable, bus, wire, or connector, such as a micro-USB to USB connector for communicating video content and powering or recharging the battery 108. Additionally, the wireless endoscope 100 may be configured without the battery 108 and instead may be powered and display video content through a positioner, the wireless device 112, or computing device 114. For example, if the medical professional operates the endoscope wirelessly thereby draining the battery 108, the wireless endoscope 100 may be connected to the computing device 114 for powering the wireless endoscope 100 and any additional power requirements while simultaneously charging the battery 108 for subsequent wireless usage. In another embodiment, the wireless endoscope 100 may be capable of being directly charged by, e.g., a wall outlet or other stationary or semi-stationary form of power supply like a charging cradle. Another embodiment may include inductively charging or powering the wireless endoscope 100 with a positioner powered by AC or DC current.

In one embodiment, the camera 102, light 104, transceiver 106, and battery 108 may be interconnected by magnetic leads (not shown). The magnetic leads may automatically align and attach the components when placed in proximity to one another. The magnetic leads may include contacts for power, logic, or command signals, as well as video communications between each component. In another embodiment, leads, wires, contacts, or connectors may be built into the case 101 for communicating power, video, control signals, or other signals between the camera 102, transceiver 106, and battery 108 which may also include contacts or leads for interfacing with the case 101.

In another embodiment, the camera 102, transceiver 106, and battery 108, and other described components may communicate signals utilizing ports, contacts, adapters, or male and female connectors. For example, the connectors may be a reduced size version of a mini-DIN, S-video, DVI, USB, coaxial, or HDMI connectors (micro video connectors). For example, the connectors may have a footprint of 0.25 mm-1 cm (diameter, area, length, etc.), however, larger and smaller footprints are also possible. In addition, the diameter of the wireless endoscope 100 may vary between 0.1 mm and 1.5 cm with other sizes being produced for different applications.

The components of the wireless endoscope 100 may include longitudinal or lateral ridges, notches, rails, guides, keyways, or other alignment structures for properly aligning a component, such as the light 104 and camera 102 within the transceiver 106 and battery 108. For example, a ridge (not shown) along the top of the cylindrically-shaped camera 102 may prevent the camera 102 from being inserted in the light 104 except when properly aligned. Similar ridges may be included on the light 104, transceiver 106, battery 108, and logic if present. A corresponding notch or ridge on the case 101 may align the components and ensure electrical connection between each component. In another embodiment, the case may configured so that the alignment of certain notches, ridges, etc., places components in electrical connection with each other and prevents other certain components from being connected together.

In another embodiment, portions or components of the wireless endoscope 100 may be separated or interconnected by flexible connectors (not shown) (e.g., centipede or corrugated configuration) that allow distinct components or portions of the wireless endoscope 100 to be individually angled and positioned. For example, wired connectors between each component of the wireless endoscope 100, such as a bus configured to communicate video signals and power, may enhance flexibility. Magnets may also be placed at each joint or in the middle of each section for positioning and retaining the wireless endoscope 100 in a desired configuration. For example, the light 104 and camera 102 portion of the wireless endoscope 100 may be angled a particular direction, relative to the remainder of the wireless endoscope 100, before insertion into the nose to view a selected sinus. The separated flexible portions of the wireless endoscope 100 may be manually adjusted or controlled by one or more servos. In one example, a mechanical pivot that provides resistive adjustments may be articulated to achieve the desired configuration of the wireless endoscope. For example, a graphical user interface accessible through the computing device 114 may be utilized to receive user selections or commands to pivot or rotate the portion of the wireless endoscope 100 including the camera 102 and light 104.

The electrical components of the wireless endoscope 100 may be manufactured utilizing processes for plastic, organic, and inorganic semiconductors, substrates, electronics, and logic. For example, the light 104, transceiver 106, battery 108 may include flexible plastic-based substrates that function with printable conductive inks, organic light-emitting diode (OLED) layers and materials, and/or active-matrix thin-film-transistor arrays. Multilayer composite structures may be utilized to create and manufacture the wireless endoscope 100. For example, roll-to-roll processing with inkjet printing or spray deposition may be utilized to produce the flexible and reduced footprint components of the wireless endoscope 100. In one embodiment, the entire wireless endoscope 100 may be configured to flex to be moved and positioned to the correct location. Magnetic coupling, wires, and MEMs connections may be utilized to bend and flex the wireless endoscope 100.

The wireless endoscope 110 may include the magnet 110 for magnetically securing the wireless endoscope 110 within the body of the patient. The case 101 may also be utilized to angle and position wireless endoscope 110 as needed by bending, flexing or by magnetically articulating into a desired configuration.

FIG. 2 is a schematic, side-view of a light 104 and camera 102 in accordance with an illustrative embodiment. In one embodiment, the camera 102 is cylindrically shaped and is inserted or partially encased in the light 104. The light 104 may be doughnut, or annular, shaped and configured to receive the camera 102. During assembly of the various parts, the light 104 and camera 102 may be changed out as has previously been described.

In another embodiment, the camera 102 and light 104 may both be stacked or placed side by side. Alternatively, the camera 102 and/or light 104 may utilize different shapes, such as an ellipse, semi-circle, square, rectangle, or oval.

FIGS. 3 and 4 are schematic front end views of the wireless endoscope 100 in accordance with illustrative embodiments. FIG. 3 illustrates the wireless endoscope 120 shaped as an oval. The light 104 may be formed from boomerang-shaped lights or lens. The light 104 may emit a single spectrum of light or distinct spectra depending on the needs of the medical professional. For example, an upper portion 106 of the light may be a miniaturized halogen light configured to emit a bright white light and the lower portion 108 of the light may be an infrared LED that may be activated as needed. In one embodiment, the light 104 and camera 102 may directly abut each other. In another embodiment, any number of spacers or separators may be built into the case 101, camera 102, or light 104 to correctly position the various components.

FIG. 4 illustrates the wireless endoscope 100 of FIG. 2 with a camera 102 and a surrounding light 104. The light 104 may be a single light source or may be composed of multiple lights that transmit light or signals at different frequencies or intensities. For example, different lights may be turned on at different times to examine cartilage, bone, blood flow, skin, or other forms of tissue. In one embodiment, the camera 102 may fixedly or movably extend or protrude from the end of the wireless endoscope 100 to provide an uninhibited view of the surroundings or specific portions of the body during use.

In one embodiment, the camera 102 may be connected to a motor that allows the camera 102 to extend a small distance from the end of the wireless endoscope 100, rotate, and/or pivot. For example, the case 101 may include bearings or rollers or a sealed slide casing (not shown) for extending and rotating the camera 102. The motor may be controlled remotely utilizing logic included in the wireless endoscope 100. For example, the wireless device 112 of FIG. 1 may include a graphical user interface for rotating or pivoting the camera 102, extending the camera 102, switching between various light sources and light spectrums, and recording video content. In addition, the camera 102 may be able to zoom in and out. In one embodiment, the camera 102 may utilize a fly eye configuration to acquire multiple views.

FIG. 5 illustrates another embodiment of a wireless endoscope 500 in accordance with another embodiment. The wireless endoscope 500 may include a case 502, first end 504, camera 506, light 508, cable 510, transceiver 512, and battery 514. The wireless endoscope 500 is externally connected to the transceiver 512 and battery 514. As a result, the size of the wireless endoscope 500 may be reduced even further.

In one embodiment, the cable 510 of the wireless endoscope 500 is attached to or incorporated into an elastic, Velcro band, or securing component. The cable 510 may include a video cable for communicating a video signal to the transceiver 512 as well as a wire for providing power. The transceiver 512 and battery 514 may be attached or integrated into the securing component (e.g., elastic band). For example, the Velcro band may include a pocket for inserting the transceiver 512 and battery 514, and the cable 510 may be built in. In one embodiment, the transceiver 512 may also include a port (not shown) for connecting the wireless endoscope 500 to a wireless device or computing device to view the video content and perform the medical procedure with the visual assistance of the wireless endoscope 500.

The first end 504 of the wireless endoscope 500 may have a diagonal or tapered cross section with a concave shape for preventing blood, mucous, pus, or other fluids from accumulating on the first end 504 thereby blocking the view of the camera 506 and the output of the light 508. Blood that accumulates on the first end 504 preferably runs to the bottom or side of the wireless endoscope 500 because of the shape.

In another embodiment, the first end 504 may be rounded with an even concave shape that pushes or maintains an air bubble in front of the first end 504 of the wireless endoscope 500 during utilization keeping the camera 506 unobstructed. The first end 504 may also be configured of a non-wettable material, a hydrophic material or a material having a lower surface tension to encourage fluids to flow off the first end 504.

Figure 6:
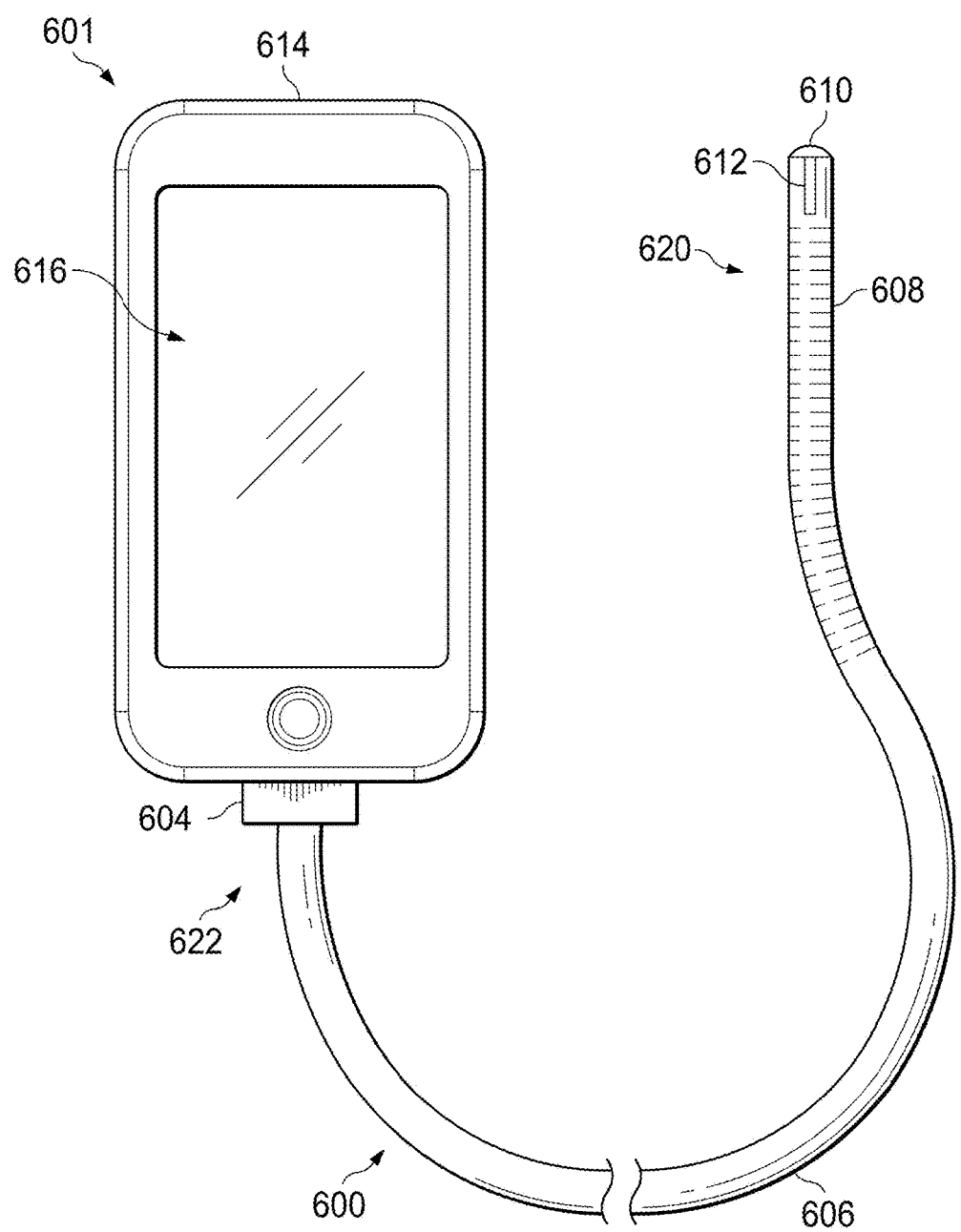
FIG. 6 is a schematic, pictorial representation of an endoscopic peripheral and system in accordance with an illustrative embodiment.

FIG. 6 is a schematic, pictorial representation of an endoscopic peripheral 600 in accordance with an illustrative embodiment. In one embodiment, the endoscopic peripheral 600 is part of an endoscopic system 601. The endoscopic system 601 may be utilized to illuminate, capture, view, and manage captured content. The endoscopic system 601 may be utilized for self-examination or to examine others based on the circumstances.

The endoscopic system 601 may be sold to individual users for performing self-examinations or examinations of others. For example, users in remote locations, such as rural users, military users, campers, or so forth, may utilize the endoscopic system 601 to do examinations, perform analysis, or so forth. The endoscopic system 601 may also be utilized to perform an after-hours examination or an examination based on specific instructions from a medical professional. In one embodiment, the endoscopic peripheral 600 may be configured to automatically display, store, and communicate content.

In one embodiment, the endoscopic system 601 includes a plug 604, a flexible cord 606, a bending portion 608, a camera 610, a light 612, a wireless device 614, and an application 616. The camera 610, the light 612, and the bending portion 608 may also be referred to as a first end 620 and the plug 604 and/or a portion of the flexible cord 606 may also be referred to as a second end 622. In one embodiment, all or portions of the endoscopic peripheral 600 may be replaceable or interchangeable. For example, the bending portion 608 may be replaced with a straight fixed or straight curved end for visualizing a patient's throat or nose. The first end 620 or the second end 622 may also be replaced due to damage or to use a different style or type of plug 604. In one embodiment, the endoscopic peripheral 600 may include plugs or interfaces separating the first end 620 and second end 622 from the flexible cord 606.

The endoscopic peripheral 600 may include a fixed or rigid housing or case for encompassing the enclosed components and connections, such as those described in the first end 620. In another embodiment, the components of the endoscopic peripheral 600 are integrated, fit together, interconnected or adhered. In yet another embodiment, the components of the endoscopic peripheral 600 are substantially enclosed by an exterior covering (e.g., a sheath) or surface of the flexible cord 606. All of the components of the camera 610 and light 612 are not covered to maintain the necessary functionality as is described herein. However, certain optically suitable coverings, sheaths, or a surface of the flexible cord 606 may be used to cover the components, such as those described for use with the first end 504.

The plug 604 may be embodied in any number of configurations. For example, the plug 604 may represent any number of standardized or proprietary connectors. The plug 604 may include any number of pins or contacts for interfacing with electronic devices. Wires, paths, connectors, or conductors within the flexible cord 606 may communicate the captured video content to the plug 604 for communication to an interconnected electronic device, such as the wireless device 614.

In another embodiment, the plug 604 may be plugged into an adapter (not shown) that may be directly connected to the applicable computing or communications device. The adapter may be especially useful for situations where the flexible cord 606 is not long enough. For example, the plug 604 may be a USB plug (e.g., USB 1.x, 2.x, 3.x, 4.x, type A, B, etc.), and the adapter may be configured to adapt the USB connection to other plug interfaces, such as a standard USB (Type A, B), micro-USB, mini USB, USB On-The-Go, lighting, Apple connectors, or so forth. However, the plug 604 may be any standard (e.g., GSMA trade association approved) or proprietary plug for communicating with computing or communications devices provided by known manufacturers and service providers (e.g., Apple, Samsung, RIM, Qualcomm, ZTE, LG, Amazon, Huawei, Google, HTC, Nokia, Microsoft, Sony, Ericcson, Dell, Acer, Lenovo, NEC, Kyocera, Mitsubishi, Panasonic, Sanyo, Sharp, Alcatel, Toshiba, etc.). In another embodiment, the adapter may be a wireless transceiver for communicating with the wireless device 614 or a computing device through a wireless connection, such as Bluetooth, Wi-Fi, Zigbee, near field communication (NFC), WiMAX, PCS, GSM, CDMA, GPRS, infrared, a proprietary connection, or so forth. Any number of FCC, FDA, IEEE, ISO, CEN, ETSI, ARIB, ANSI, or IEC approved wireless communications protocols or standards may also be transmitted by the endoscopic peripheral 600 or the adapter. The wireless adapter may also include logic for encoding, formatting, and processing signals to and from the wireless device 614. The wireless adapter may be utilized for applications where the standard cord length is insufficient or the environment is otherwise incompatible.

The length of the flexible cord 606 may vary based on the application. For example, the flexible cord 606 may vary between 6 cm to 5 meter in length. The endoscopic peripheral 600 may also be utilized with a repeating, telescoping or extension device to extend the length of the flexible cord 606. In one embodiment, the flexible cord 606 shields and protects the twisted pairs, wires, or cabling encompassed within the endoscopic peripheral 600. The exterior or outer surface of the flexible cord 606 may be composed of plastic, rubber, or another protecting material. For example, the flexible cord 606 may represent medical grade plastic that may be more easily cleaned and sterilized for repeated use. In one embodiment, the flexible cord 606 may include an outer, secured or strippable protective layer, a shield (or shielding), an electrostatic shield, insulation, and one or more conductors or electrical contacts configured to communicate power, image content, and control signals. For example, the electrostatic shield may a jacketed wire mesh configured to reduce electronic noise and interference.

The bending portion 608 is configured to be bent or positioned and thereafter hold the position. For example, the user may position the bending portion 608 in an arcuate shape that may facilitate looking into the mouth of an individual. In one embodiment, the bending portion 608 may be linked to controls (not shown) or a motor (not shown) for controlling the motion, angle, or position of the bending portion and displayed on the endoscopic system 601 for articulating the bending portion 608 relative to its surroundings. For example, a directional controller may be configured to move the camera 610 and light 612 to a particular direction, position, or angle. In another embodiment, the bending portion 608 may be flexible enough to deform based on the provided space and configuration in which the endoscopic peripheral 600 is being utilized. The flexible cord 606 may also include a tapered portion for relieving pressure or stress at the point of insertion or on the surrounding tissue. For example, the outer diameter or cross section of a desired portion or length of the flexible cord 606 may be smaller than the bending portion 608, or vice-versa.

The camera 610 may be a video or still image capturing device as was previously described. In one embodiment, the camera 610 is a miniaturized camera inserted or housed in the tip of the endoscopic peripheral 600 and configured to communicate the captured content through a wire, bus, cable or so forth. In one embodiment, the camera 610 may include a processor, DSP, ASIC, graphics rendering chip, or other processing unit or circuit for processing the captured images. In another embodiment, the camera 610 may communicate the raw captured content to a separate electronic device for processing. The camera 610 may also represent a fiber optic camera with processing components at the second end 622 near, attached to or integrated with the plug 604. The endoscopic peripheral 600 may be configured whereby different camera types and styles may be removably inserted or housed in the tip of the endoscopic peripheral 600.

In one embodiment, the endoscopic peripheral 600 may include an integrated or externally connected thermometer (not shown). For example, the first end 620 may be configured with a thermometer (not shown). By way of another example, the camera 610, light 612, or bending portion 608 may include an integrated thermometer (not shown). The thermometer may be a digital thermometer utilized to accurately determine a user's temperature and display the information to the wireless device 614. However, the thermometer may be a mercury-in-glass thermometer, infrared thermometer, or liquid crystal thermometer that may be utilized to check temperature as well as determine whether an individual has a fever or is hypothermic. The endoscopic peripheral 600 may be configurable from a non-thermometer version to one having any one of the aforementioned thermometer types. A thermometer may be removable inserted or housed, for example, in the camera 610, light 612 or bending portion 608.

The described embodiments of the endoscopic peripheral 600 and wireless endoscope are configured to be universal plug-and-play devices for both computing, communications, and other electronic devices. In one embodiment, the endoscopic peripheral 600 is hot pluggable and configured for zero configuration connections. For example, when physically or wirelessly connected to an electronic device, the endoscopic peripheral 600 or wireless endoscope may automatically establish working configurations with other devices, such as computing, communications, or other electronic devices. The plug-and-play standards comply with applicable wired or wireless standards set by the Universal Plug and Play (UPnP), ISO, IEEE (e.g. 802.11X, 802.14X, DICOM, MIB, Personal Health Data (PHD), and so forth. Combined standards or proprietary standards may also be utilized.

In another embodiment, the wireless device 614 (or a computing device) may include a processor, memory, and other hardware, firmware, and software that are specifically designed to interoperate with the endoscopic peripheral 600 and its one or more described components. The endoscopic peripheral 600 may also include a processor and memory. The processor is circuitry or logic enabled to control execution of a set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks. For example, the processor may perform encoding of standard or high definition content captured by the camera 610 to reduce latency when communicating or viewing the content. In another example, the content may be raw, encoded, or formatted content that is processed by the interconnected electronic device, such as the wireless device 614.

The processor may be a single chip or integrated with other computing or communications elements. The memory may be a hardware element, device, or recording media configured to store data for near immediate retrieval, subsequent retrieval or access at a later time. The memory may be static or dynamic memory. The memory may include a hard disk, random access memory, cache, removable media drive, mass storage, or configuration suitable as storage for data, instructions, and information. In one embodiment, the memory and processor may be integrated. The memory may use any type of volatile or non-volatile storage techniques and mediums.

In one embodiment, the endoscopic peripheral 600 may include a memory to store content captured by the camera 610. For example, each new examination session may be saved as a discrete file that may be communicated, accessed, or retrieved later. The memory may also store an application that is utilized to interface the endoscopic peripheral 600 with the wireless device 614. For example, a program, script, sub-routine, set of instructions, or so forth may be stored in the memory so that when the endoscopic peripheral is plugged into an electronic device, the electronic device is configured to decode, process, format, and view the captured content as well as manage functionality of the endoscopic peripheral 600. The user may utilize the wireless device 614 to turn the endoscopic peripheral 600 on and off, adjust the light intensity, resolution, video/image characteristics (e.g., compression, format, brightness, contrast, frames, aspect ratio, etc.), physically angle the camera or lights, adjust or turn on and off different sets of lights, automatically stream content, store content on the endoscopic peripheral 600, wireless device 614, or other component.

The wireless device 614 may include any number of hard keys or soft keys. The hard keys are dedicated buttons or interface elements hard-coded for a single, unique, and consistent purpose. Examples of hard keys include the 12-buttons of the traditional alpha-numeric keypad, the send/end keys commonly found on mobile phones, and buttons to initiate or end a speakerphone function. The soft keys are programmable buttons or interface elements. Soft keys are usually located alongside a display device and may perform different functions dependent on the text shown near the soft keys on the display. Examples of soft keys may include a power button for the endoscopic peripheral 600.

The wireless device 614 may include any number of computing and telecommunications components, devices or elements which may include busses, motherboards, circuits, ports, interfaces, cards, converters, adapters, connections, transceivers, displays, antennas, and other similar components. For example, the wireless device 614 may represent a voice over Internet protocol (VoIP) phone, plain old telephone system (POTS) telephone, e-reader, or so forth that may receive and/or communicate the content captured by the camera 610.

In one embodiment, the content captured by the endoscopic peripheral 600 may be communicated to, through, or by a portal or other software or hardware interface. The portal may be a web site that functions as a central point of access to information on the Internet or an intranet. The portal may be accessed from any computing or communications system or device enabled to communicate through a network connection. The endoscopic peripheral 600 may have a hardware or software identifier that is utilized to automatically route captured content to the portal for viewing, storage, management, or so forth.

Figure 7:
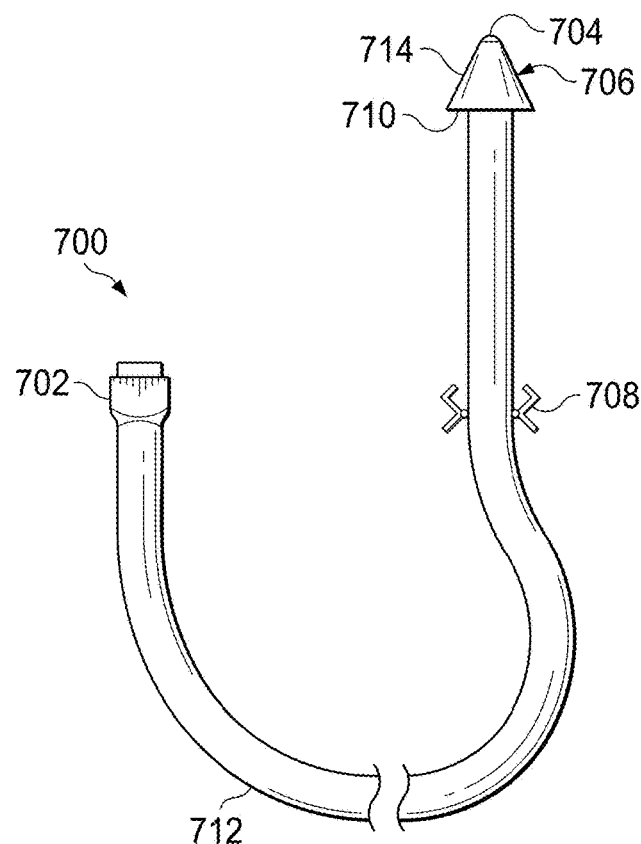
FIG. 7 is a schematic, pictorial representation of another endoscopic peripheral in accordance with an illustrative embodiment.

FIG. 7 is a schematic, pictorial representation of another endoscopic peripheral 700 in accordance with an illustrative embodiment. The endoscopic peripheral 700 may include a micro USB plug 702, a camera 704, a funnel shaped head 706, and a latch 708.

In one embodiment, the endoscopic peripheral 700 may include a micro USB plug 702. The micro USB plug 702 may be configured to be inserted into a computing or communications device. For example, many smart phones include micro USB connectors that may be configured to communicate with the endoscopic peripheral 700. However, the micro USB plug 702 may be replaced by any miniaturized plug whether standardized or custom designed. The endoscopic peripheral 700 may also include as a standard accessory one or more adapters for converting the plug, such as the micro USB plug 702, to a different standard or format, such as USB.

In another embodiment, the adapter (not shown) may be a wireless transceiver. The wireless transceiver adapter may include a rechargeable battery and may be configured to communicate with computing or communications devices utilizing Bluetooth, Wi-Fi, near field communications, Zigby or other communications standards, protocols, or formats.

In one embodiment, a body 712 of the endoscopic peripheral 700 may include any number of strengthening, shielding, or impact resistant components. For example, the body 712 or cord portion of the endoscopic peripheral 700 may include a wire or plastic framework both surrounding, insulating and shielding the wires within the body 712. As a result, the body 712 may be shielded from radio frequency signals and other electronic noise that are common in the various environments in which the endoscopic peripheral 700 will be utilized. In addition, the reinforcements to the framework of the body 712 may prevent the framework material around from stretching, tearing, or sustaining excess wear due to repositioning or otherwise moving the endoscopic peripheral 700. For example, the body 712 may be long enough that a medical professional may occasionally step on or run over the body 712 with an office chair, impact or otherwise apply pressure and strain on the endoscopic peripheral 700 which it is configured to withstand without losing functionality.

In one embodiment, the endoscopic peripheral 700 may include the funnel shaped head 706. The camera 704 may be placed at the tip of the funnel shaped head 706 for visualizing a patient's ear, nose, or other organ or body portion. The funnel shaped head 706 may be configured as a safety feature for the endoscopic peripheral 700. For example, the increased angle of the sides 714 and widening end 710 of the funnel shaped head 706 may ensure that a user does not insert the endoscopic peripheral 700 too far into a patient's body. For example, the funnel shaped head 706 may prevent the user from damaging a patient's eardrum when trying to visualize a potential medical issue in the patient's ear. In three-dimensions, the funnel shaped head 706 is conically shaped with the camera 704 at the tip of the head. The length and angle of the tapered sides 714 of the funnel shaped head 706 may vary. For example, the sides 714 of the funnel shaped head 706 may be elongated for viewing the sinuses of a patient or may be shorter for viewing the ear of a patient.

In one embodiment, sides 714 of the funnel shaped head 706 may be curved or arced to have a steep or shallow taper to select an insertion depth for the funnel shaped head 706 within the patient. The funnel shaped head 706 of the endoscopic peripheral 700 may also be rigid or flexible. The funnel shaped head 706 and the camera 704 may be replaceable or attached to the body 712 for customization. For example, the shape and size of the funnel shaped head 706 may vary for pediatric, adult, and animal usage. For example, the sides 714 of the funnel shaped head 706 may be configured with a shallow taper terminating in a wide end 710 for visualizing children's eardrums when compared with a funnel shaped head 706 that may be utilized to visualize the sinuses of a horse.

In another embodiment, the ends 710 of the funnel shaped head 706 may include a protuberated portion, extension or a collar that is integrated with or attached to the funnel shaped head 706 at the end 710 to prevent over-insertion or extension of the endoscopic peripheral 700 in the patient's body during utilization. The endoscopic peripheral 700 may include one or more latches 708 for securing a disposable cover or sheath (not shown). For example, the latch 708 may be configured to hold a securing ring 806 (shown in FIG. 8 and described below).

In another embodiment, the latch 708 may be one or more hooks or extensions hingedly, removably or pivotally attached around or to the body 712 to secure or receive the securing ring of the disposable cover. The latch 708 may also include a release for removing the disposable cover from the latch 708. As a result, the disposable cover is secured in place during utilization and easily attached and removed when working with a number of patients, such as in the clinical or emergency setting. As previously disclosed, the funnel shaped head 706 ending may be configured in different shapes and sizes for varying applications. For example, the funnel shaped head 706 may be formed of a flexible plastic, rubber, or supple material that is less likely to injure a patient during a rigorous examination. The disposable cover may also include a swabbing section for swabbing a body part for analysis (e.g., swabbing the users nasal pages, tonsils, throat, cheek, etc.). The swabbing section may be formed of an absorbent material, such as a polyester knit fabric, adhered to, woven as part of or integrated with the disposable cover.

Figure 8:
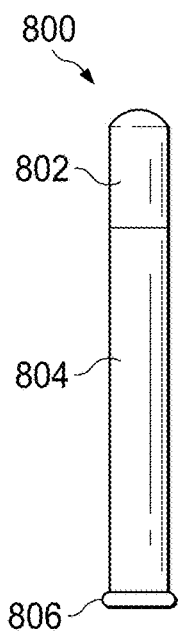
FIG. 8 is a schematic, pictorial representation of a disposable cover for an endoscopic peripheral in accordance with an illustrative embodiment.

FIG. 8 is a schematic, pictorial representation of a disposable cover 800 for an endoscopic peripheral in accordance with an illustrative embodiment. The disposable cover 800 may be utilized for any number of medical or surgical instruments or for other devices, systems, and applications. For example, the disposable cover 800 may be utilized on a borescope in a clean room of a semiconductor manufacturing facility. In one embodiment, the disposable cover 800 includes a generally rigid portion 802, a flexible portion 804, and a securing ring 806.

In one embodiment, the disposable cover 800 includes two or more sections or portions including at least the rigid portion 802 and the flexible portion 804. In other embodiments, the disposable cover 800 may be formed entirely of rigid or flexible materials corresponding to the rigid portion 802 and the flexible portion 804, respectively.

The rigid portion 802 may be composed of a clear optically transparent material for enabling a camera of the endoscopic peripheral to gather image and video content. The rigid portion 802 may also include a variation of built-in lens configuration for viewing an area at the viewing end for enhancing the images captured by the camera. For example, the rigid portion 802 may be formed of a clear plastic, such as a U.S. Pharmacopeia (USP) Class V and VI silicon, rubber, polymers, or plastic materials (or a combination thereof).

In one embodiment, the flexible portion 804 may composed of latex, Vytex, resin (e.g., AT-10 resin) plastic, polyurethane, polyisoprene, nitrile, or so forth. The flexible portion 804 may allow the disposable cover 800 to bend, flex, or deform with the motion of the endoscopic peripheral.

For example, the endoscopic peripheral may be configured to bend as much as 90-360°. The disposable cover 800 may flex with the endoscopic peripheral to protect the patient (e.g., tissues, membranes, organs, blood, etc.) and prevent contamination of the endoscopic peripheral.

The rigid portion 802 and the flexible portion 804 may be connected or bonded in any number of ways. In one embodiment, the flexible portion 804 is crimped within an end of the rigid portion 802. In another embodiment, the rigid portion 802 is heat bonded to the flexible portion 804. In another embodiment, the rigid portion 802 and flexible portion 804 are adhered or welded to one another.

In another embodiment, the disposable cover 800 may be formed entirely of a rigid plastic material. A rigid cover may be particularly useful for embodiments of the endoscopic peripheral that are rigid or otherwise fixed.

Figure 9:
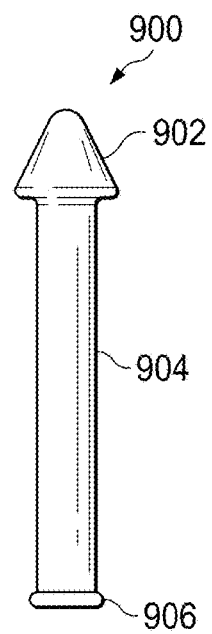
FIG. 9 is a schematic, pictorial representation of a disposable cover for an endoscopic peripheral in accordance with an illustrative embodiment.

FIG. 9 is a schematic, pictorial representation of a disposable cover 900 for the endoscopic peripherals in accordance with an illustrative embodiment. In one embodiment, the disposable cover 900 of FIG. 9 may be configured to be utilized with the endoscopic peripheral 700 of FIG. 7. The head portion 902 may be configured to be positioned over the funnel shaped head. Similarly, the shaft portion 904 may be flexible and expandable allowing the disposable cover 900 to be pulled over the funnel shaped head 706. In one embodiment, the securing ring 906 may be expanded to fit over the funnel shaped head when being positioned. For example, the securing ring 906 may include a broken or split section formed, for example, by a split ring for allowing the securing ring 906 to deform or open to receive the funnel shaped head 706. The securing ring 906 may also be configured to include a separable compression ring (not shown) for allowing the securing ring 906 to deform, whereby the compression ring may be placed over either end of the endoscopic peripheral 700 and secured over the securing ring 906.

In another embodiment, the securing ring 906 may be a fortified or reinforced section of the disposable cover 900. For example, the material making up the disposable cover 900 may be formed (e.g., compressed, molded, extruded, shaped, etc.) into a substantive solid ring forming the securing ring. The disposable cover 900 may include one or more reinforced holes or annular ribs (not shown) for attaching to one or more latches, hooks, or extensions of the endoscopic peripheral 700. The disposable cover 900 and fortified holes may be integrally formed, such that the disposable cover 900 does not rip, tear, rupture, or break during utilization, placement, removal, or so forth.

In alternative embodiments, the securing ring 906 may be configured to actively secure the disposable cover 900 to the endoscopic peripheral 700, surgical device, medical instrument, or other tool. For example, the securing ring 906 may be configured as a collapsible or drawable circumference, such as a miniaturized wire tie, drawing strings, buckle, or clamp. The securing ring 906 may be formed of a non-slip material that allows it to be tightly drawn against the endoscopic peripheral 700 or other device without slipping during utilization. A portion of the endoscopic peripheral 700 to which the securing ring 906 is attached may also be configured with a non-slip feature or formed of a non-slip material to help keep the disposable cover 900 in place. As a result, the securing ring 906 may be easily unlatched, unbuckled, uncinched, or cut when its purpose is fulfilled and needs to be disposed of. The disposable cover 900 may be a stand-alone embodiment for utilization with a number of different devices and tools. The size (e.g. length, diameter, etc.) and shape (e.g., circular, square, or oblong cross sections, differently sized head, body, opening, and end, etc.) of the disposable cover 900 may correspond to the medical device or tool as is herein described.

Figure 10:
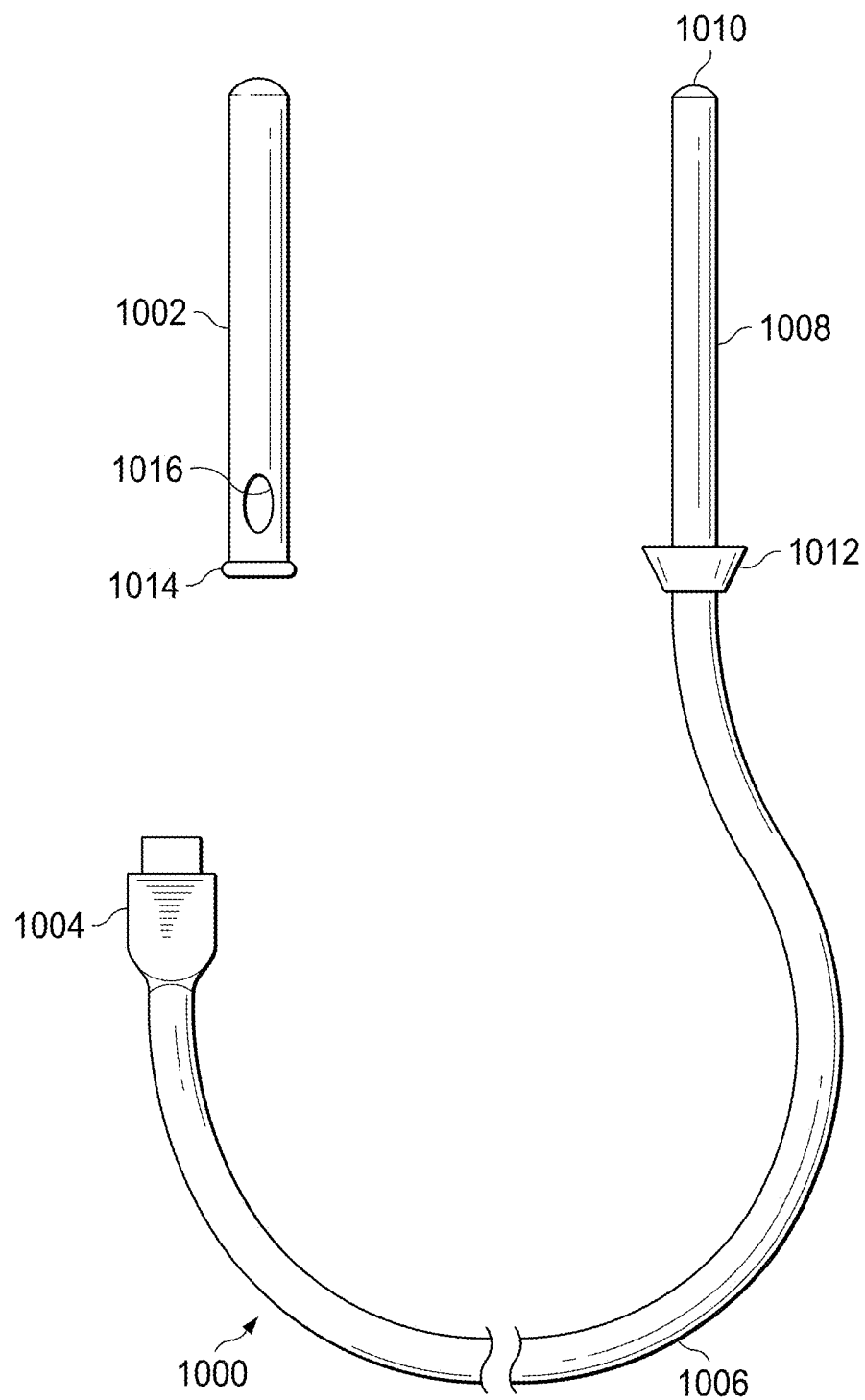
FIG. 10 is a schematic, pictorial representation of a plug-and-play endoscopic peripheral and a cover in accordance with an illustrative embodiment.

FIG. 10 is a schematic, pictorial representation of a plug-and-play endoscopic peripheral 1000 and a cover 1002 in accordance with an illustrative embodiment. The endoscopic peripheral 1000 may include a plug 1004, a body 1006, a head 1008, a camera 1010, and a clamp 1012.

In one embodiment, the plug 1004 is a USB or other plug-and-play connector. As a result, the endoscopic peripheral 1000 may not require a special device driver or support software. For example, the implementation the USB plug (e.g., USB 2.0, 3.0, 4.0, etc.), Ethernet, FireWire, or other plug-and-play standard may allow the endoscopic peripheral 1000 to be automatically recognized by computing or communications devices. The plug 1004 may also be a proprietary connector, such as a connector for Apple devices (e.g., lightning, etc.). This may be particularly useful for users that have limited access to or experience with electronic devices, such as computers.

In one embodiment, the endoscopic peripheral 1000 may be automatically powered on and activated in response to the plug 1004 being connected to an electronic device, such as a computer or a cell phone. The endoscopic peripheral 1000 may also include a switch, button, or other selection or interface component for performing any of: powering on/off the endoscopic peripheral 1000, increasing or decreasing the light intensity (see, e.g., light 612 shown in FIG. 6), changing from video to still images, changing light spectra, adjusting resolution, adjusting video or camera settings, or so forth.

As previously disclosed, the head 1008 of the endoscopic peripheral 1000 may be rigid, semi-rigid or flexible (e.g., articulated relative to the body 1006). In one embodiment, the head 1008, together with or without the clamp 1012, may be removably attached to the body 1006 of the endoscopic peripheral 1000. The endoscopic peripheral 1000 may be configured to receive rigid, semi-rigid or flexible heads depending on the medical application. The disposable cover 1002 may similarly be rigid, semi-rigid or flexible based on the configuration of the head 1008.

The clamp 1012 is configured to removably secure the disposable cover 1002 tightly against the head 1008 and the camera 1010. The clamp 1012 may secure an end, an annular rib or a securing ring 1014 of the disposable cover 1002. The disposable cover 1002 may also include a hole 1016. The hole 1016 is a receptacle or attachment point. For example, the hole 1016 may be configured to receive a detent, catch, pawl, dog, or spring biased ball (not shown) on the head 1008 or the clamp 1012. The hole 1016 is defined by the disposable cover 1002 and may be utilized to secure disposable cover during utilization.

Figure 11:
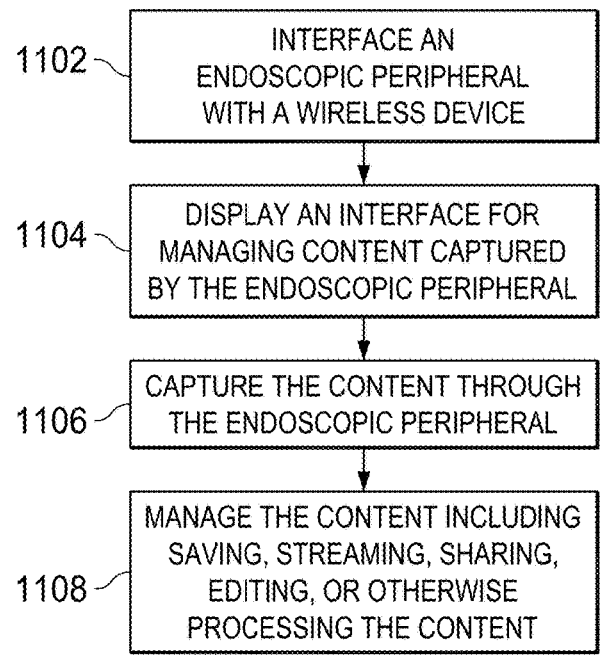
FIG. 11 is a flowchart of a process for utilizing an endoscopic peripheral in accordance with an illustrative embodiment.

FIG. 11 is a flowchart of a process for utilizing an endoscopic peripheral in accordance with an illustrative embodiment. In one embodiment, the process of FIG. 11 may be implemented by a system controlled by a user or in part by electronically utilizing an endoscopic peripheral with a computer or wireless device (utilized for purposes of simplicity). The endoscopic peripheral may include a head that is covered with a disposable cover or otherwise sanitized before being utilized.

The process may begin by interfacing an endoscopic peripheral with a wireless device (step 1102). For example, the user may have inserted a port end of the endoscopic peripheral in a computer or wireless device for capturing the images. In one embodiment, the endoscopic peripheral may be powered by the computer or wireless device. In another embodiment, the endoscopic peripheral may include a separate power supply, such as batteries or AC/DC power plug. In yet another embodiment, the endoscopic peripheral may by powered from an electrical source by wireless energy transmission. The image content may also be communicated from a camera of the endoscopic peripheral to the computer or wireless device to be viewed, processed, or saved. The endoscopic peripheral may also perform some image storage, processing, filtering, noise reduction, formatting, clean up, and other similar operations, such as before communicating the captured content to the computer or wireless device.

Next, the system displays an interface for managing content captured by the endoscopic peripheral (step 1104). In one embodiment, the interface is a program, application, or other graphical user interface that is activated in response to user input (e.g., opening an application, selecting an icon, etc.) or in response to the connector/plug end of the endoscopic peripheral being inserted in the computer or wireless device.

Next the system captures the content through the endoscopic peripheral (step 1106). The content of step 1106 may include video and image content in any number of spectra. The endoscopic peripheral may include one or more LEDs, fiber optics, or other light or spectral sources to enable the camera of the endoscopic peripheral to fully capture the desired content.

Next, the system manages the content including saving, streaming, sharing, editing, or otherwise processing the content (step 1108). In one embodiment, the interface is a graphical user interface that provides the user with managing and processing options, such as record the content, upload the content, send or share the content with a designated user, contact or device, stream the content to a designated user, contact, device, or location in real-time, or edit the content. The software utilized with the endoscopic peripheral may be standard or default software utilized by a computing or communications device or proprietary software that is automatically or manually installed in response to connecting the endoscopic peripheral for the first time. The content may be stored and then uploaded to a designated location specified by the user or associated with the endoscopic peripheral. For example, video content captured by the endoscopic peripheral may be automatically uploaded to a server/database through one or more networks and then saved under an identifier associated with the endoscopic peripheral. For example, a serial number may be associated with a patient identifier. As a result, users in remote locations or at home may be able to be treated by doctors even if they do the examination themselves.

Figure 12:
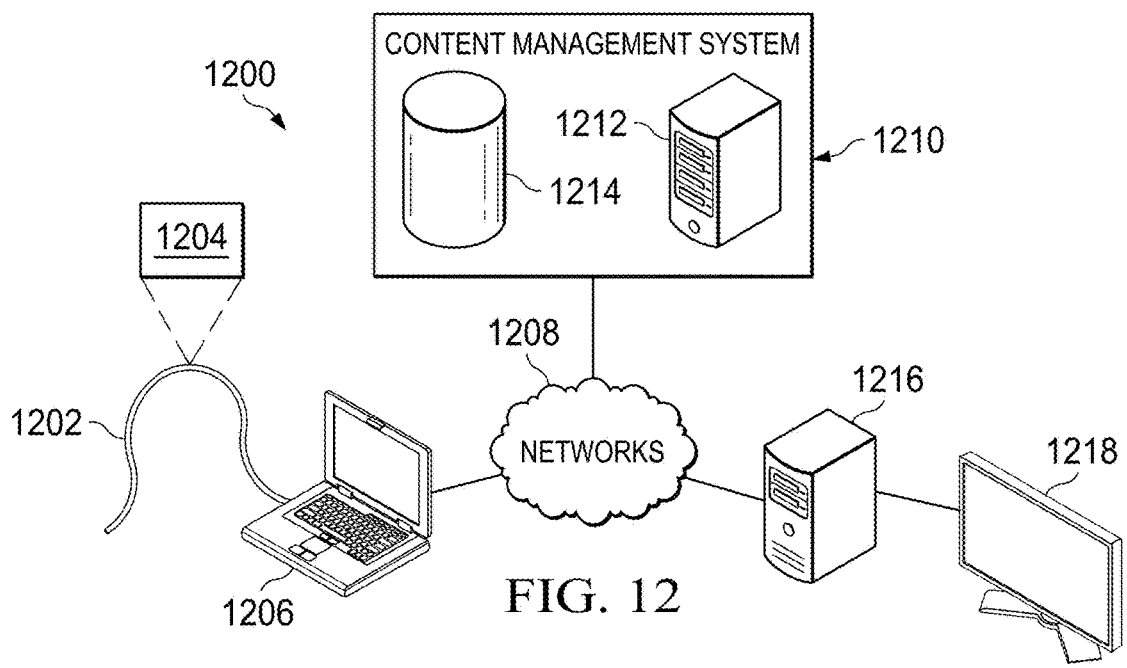
FIG. 12 is a schematic, pictorial representation of a communications environment in accordance with an illustrative embodiment.

FIG. 12 is a schematic, pictorial representation of a communications environment 1200 in accordance with an illustrative embodiment. In one embodiment, the communications environment 1200 may include an endoscopic peripheral 1202, an associated identification 1204, a laptop 1206, networks 1208, a content management system 1210, a server 1212, a database 1214, a computer 1216, and a display 1218.

The endoscopic peripheral 1202 may be configured to capture content that is subsequently streamed to a remote location whether it be the laptop 1206 or the display 1218. In one embodiment, the endoscopic peripheral 1202 may include the identifier 1204 for identifying content captured by the endoscopic peripheral 1202. The identifier 1204 may be a hardware or software identifier. For example, the identifier 1204 may be a MAC address, IP address, serial number, IMEI, or user assigned identifier, such as a name.

In one embodiment, the endoscopic peripheral 1202 includes a memory configured to store the identifier 1204. The endoscopic peripheral 1202 may be configured to be plug-and-play compatible. However, in other embodiments, the endoscopic peripheral 1202 may store scripts, updates, software, or a set of instructions and commands for utilizing and interfacing the endoscopic peripheral 1202. The endoscopic peripheral 1202 may also be configured to store captured image content. As a result, the content may be easily moved from one location to another and uploaded and communicated as needed. This may be particularly useful for remote settings, such as military operations, rural areas, triage areas, and so forth.

The laptop 1206 may utilize a default application or a specialized application to view the content captured or visualized by the endoscopic peripheral 1202. For example, any number of default video or content applications, operating systems, or so forth may be utilized to view, save, and manage the content.

The laptop 1206 or the endoscopic peripheral 1202 may communicate with the networks 1208. The laptop 1206 is representative of any number of computing or communications devices. The networks 1208 represent one or more communications networks as are herein described. The connections between the components may be wired or wireless.

Communications of content from the endoscopic peripheral 1202 may be communicated to the content management system 1210. The content management system 1210 may represent a cloud computing system, server farm, or other communications system. In one embodiment, the server 1212 may be accessed by the laptop 1206 to stream the captured content. The database 1214 may represent one or more databases storing the captured content. In one embodiment, the computer 1216 may access content captured by the endoscopic peripheral 1202 from the content management system 1210. In another embodiment, the computer 1216 may access the content from the laptop 1206 through the network 1208. A user may utilize the computer 1216 and the display 1218 to view the content captured by the endoscopic peripheral 1202. For example, the user may be a doctor remotely located from the endoscopic peripheral 1202 that has been loaned to and is being utilized by a rural patient. The content may be captured and communicated in real-time (or near/substantial real time) or as non-real time communications.

In one embodiment, the endoscopic peripheral 1202 or software stored in or associated with the endoscopic peripheral 1202 may be configured to automatically communicate with the content management system 1210 (or respective components) or the computer 1216. The communications may be routed utilizing a hardware address or software address, such as a MAC address, IP address, website, secured tunnel, or so forth.

Figure 13:
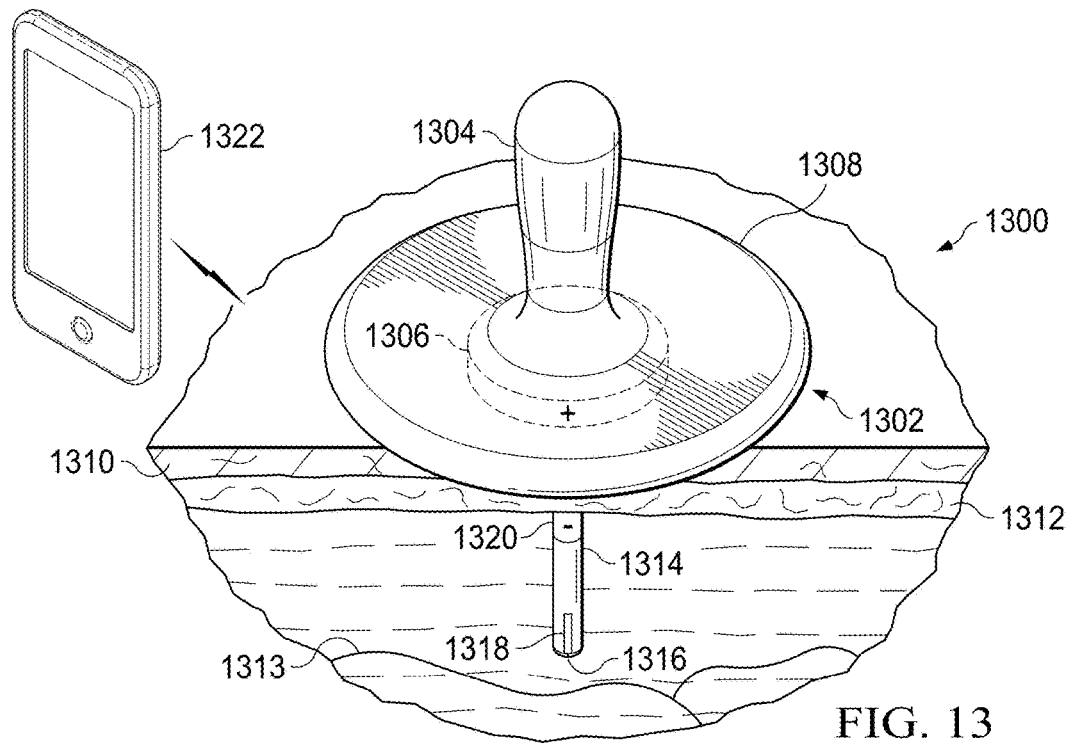
FIG. 13 is a schematic, pictorial representation of an endoscopic system in accordance with an illustrative embodiment.

FIG. 13 is a schematic, pictorial representation of an endoscopic system 1300 in accordance with an illustrative embodiment. The endoscopic system 1300 may include any number of components, devices, or equipment. In one embodiment, the endoscopic system 1300 may include a positioner 1302. The positioner 1302 may further include a handle 1304, a magnet 1306 and a surface contact 1308.

The endoscopic system 1300 may be utilized to wirelessly and magnetically function through skin 1310, tissue 1312, to view internal portions of the body, such as the organs 1313. The endoscopic system 1300 may further include a wireless endoscope 1314 including a camera 1316, a light 1318, and a magnet 1320. In one embodiment, the wireless endoscope 1314 may be placed beneath the skin 1310 and tissue 1312 to view an internal body cavity or portions of the body, such as the organs 1313.

For example, the wireless endoscope 1314 may be inserted into the body through a natural opening or surgically created opening. For example, the wireless endoscope 1314 may be inserted through the belly button during a laparoscopic procedure. The size of the wireless endoscope 1314 may vary dramatically based on the type of analysis, surgery, or other medical procedure being performed utilizing the endoscopic system 1300. For example, the size of the wireless endoscope 1314 may vary between 0.25 centimeters and approximately 2 inches in length with a diameter of approximately 0.25 centimeters to 2 centimeters. However, any number of different sizes, shapes, and configurations are envisioned for the wireless endoscope 1314.

In one embodiment, the wireless endoscope 1314 may directly communicate wirelessly with a wireless device 1322 (e.g., Bluetooth, Near Field Communications, etc.). However, the wireless endoscope 1314 may communicate with the wireless device 1322 through any number of intermediary networks, devices, adapters, or so forth. For example, the positioner 1302 may include a wireless transceiver (not shown) to receive the image signals from the wireless endoscope 1314 and communicate or relay those signals to the wireless device 1322. As a result, the positioner 1302 may include a processor, memory, specialized logic, or software for communicating with both the wireless endoscope 1314 and the wireless device 1322. In addition, the wireless endoscope 1314, positioner, or wireless device 1322 may be configured to store, format, encrypt, decode, or otherwise process the captured content for communication and viewing as is known in the art.

The positioner 1302 may be utilized to magnetically secure, move, and position the wireless endoscope 1314. In one embodiment, the positioner 1302 may include the magnet 1306 of a first polarity configured to attract the magnet 1320 of the wireless endoscope 1314 that is of a different polarity. The magnet 1306 may be oriented relative to, embedded within or attached to the bottom of the surface contact 1308 to ensure that a strong magnetic field and forces are communicated through the skin 1310 and the tissue 1312 to attract and secure the wireless endoscope 1314. The magnet 1306 may be configured, at least partially, within the handle 1304 and oriented so that an end or side or the magnet 1306 terminates at the surface contact 1308. The magnets 1306 and 1320 may be integrated with the respective components or may be attached, secured, or housed based on the medical procedure, circumstances or conditions. For example, magnets of different strengths and pluralities may be required for the positioner 1302 and the wireless endoscope 1314 requiring that a user attach or connect the desired or required magnets 1306 and 1320.

In one embodiment, only the magnets 1306 and 1320 may be utilized to secure the wireless endoscope 1314. However, in other embodiments, any number of lanyards, tethers, cables, wires, or anchors may be utilized to further secure the wireless endoscope 1314 to prevent inadvertent loss, misplacement, or the need for retrieval. The positioner 1302 may have any number of shapes and configurations that facilitate the user and moving and positioning the wireless endoscope 1314. In one embodiment, the handle 1304 may be gripped by a user, robot, or other medical professional to move and position the wireless endoscope 1314. The handle 1304 may have an ergonomic shape to prevent hand cramping or fatigue and to further stabilize any motion of the positioner 1302 or form a housing for, at least partially, containing magnet 1306.

In one embodiment, the surface contact 1308 may be a flange, shroud or skirt around the periphery of the bottom of the handle 1304 that stabilizes the positioner 1302, focuses magnetic field or forces and eases movement during utilization. The surface contact 1308 may have a slippery surface known to not adhere or stick to the skin 1310 or other contact point. In other embodiments, the bottom of the surface contact 1308 may be lubricated to easily move the positioner 1302 against the body of the user. The surface contact 1308 may be wide enough or have a diameter sufficient to stabilize the positioner 1302 when not being held or gripped by the user. The positioner 1302 may also be held or moved by any number of mechanical arms or robotic components.

In one embodiment, the endoscopic system 1300 may be utilized as a secondary imaging or vision system that may be utilized to view surgical procedures being performed on or in the organs 1313 or tissue 1312. For example, the wireless endoscope 1314 may be easily moved into position and secured above an incision site on one of the organs 1313. The wireless device 1322 may also be moved or positioned to best facilitate the medical professional. The wireless device 1322 is representative of any number of computing, communications, or display devices that may display the image content, (e.g., video, still images or other content) captured by the camera 1316 as illuminated, for example, by the lights 1318.

The magnets 1306 and 1320 may represent any number of rare earth magnets, electromagnets, or other naturally occurring or artificially created magnets (or other emitters as are herein described). The magnets 1306 and 1320 (as well as magnets within the wireless endoscope 1314) may be utilized to perform magnetic imaging, such as magnetic resonance imaging nuclear magnetic resonance imaging, or magnetic resonance tomography to visualize internal structures of the body in detail. The positioner 1302 and wireless endoscope 1314 may be utilized alone or in combination to perform MRI. Both the positioner 1302 and the wireless endoscope 1314 may include magnets and sensors (not shown) for performing MRI of the portions of the body that separate the positioner 1302 and the wireless endoscope 1314 or other tissues, organs or so forth. The endoscopic system 1300 may include a number of small, but powerful emitters or magnets as well as sensitive sensors. A wired or wireless energy source may provide the power, signal, or particles for emitting the field, particles, signal, light, or so forth emitted from one or more portions of the endoscopic system.

The endoscopic system 1300 may visualize portions of the body by detecting and processing the reflectance and/or absorption of emitted fields, signals, or particles utilizing the sensors. For example, the absorption and/or reflectance characteristics of the cells, tissues, organs, bones, or other body parts may be collected by the sensors The wireless device 1322 may utilize a standard or custom application, program, operating system, or interface to communicate with the wireless endoscope 1314. For example, the wireless endoscope 1314 may be pared with the wireless device 1322 and configured to communicate through Bluetooth, WiFi, Near Field, or other communication connects between the two devices.

Figure 14:
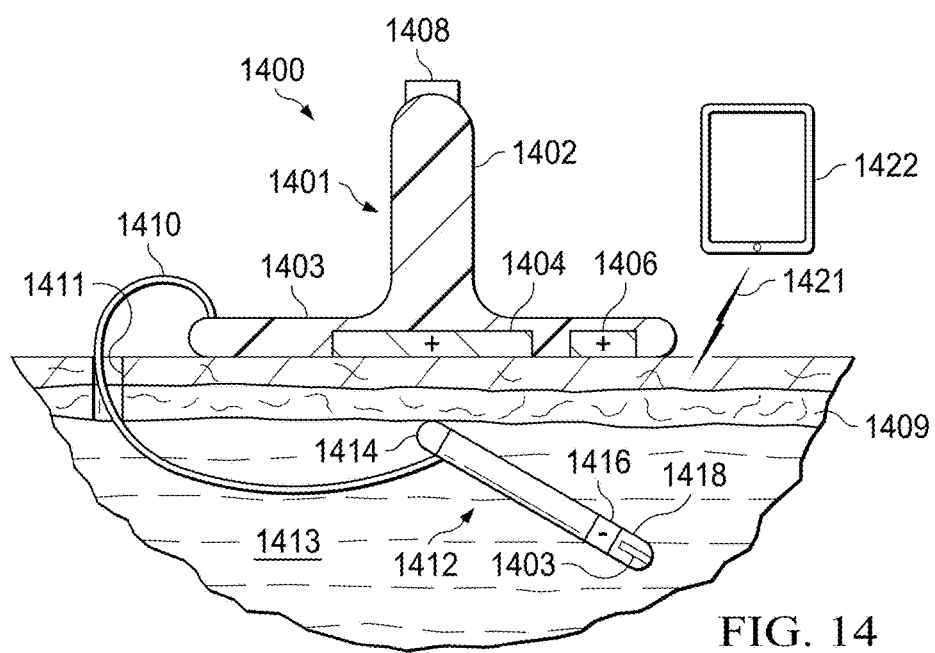
FIG. 14 is a schematic, side view of another endoscopic system in accordance with illustrative embodiment.

FIG. 14 is a schematic, side view of another endoscopic system 1400 in accordance with an illustrative embodiment. In one embodiment, the endoscopic system 1400 may include a positioner 1401, a handle 1402, a surface contact 1403, a first magnet 1404, a second magnet 1406, controls 1408, tissue 1409, a lanyard 1410, an opening 1411, a wireless endoscope 1412, a body cavity 1413, a magnetic end 1414, a camera 1418, a light 1420, a wireless signal 1421, and a computing device 1422.

The positioner 1401 may include the first magnet 1404 for attracting the magnetic end 1414 of the wireless endoscope 1412. The positioner 1401 may also include the second magnet 1406 for interacting with the magnetic collar 1416. The second magnet 1406 and the magnetic collar 1416 may be utilized to adjust the angle and direction of the wireless endoscope 1412 (i.e., the orientation of the wireless endoscope relative to its surroundings), and particularly the camera 1418.

The positioner 1401 may be rotated to further angle and position the wireless endoscope 1412. In one embodiment, the second magnet 1406 and/or the magnetic collar 1416 may be electromagnets that may be selectively turned on and off with the magnetic field being adjustable in strength when turned on. For example, the second magnet 1406 and magnetic collar 1416 may be turned off until the first magnet 1404 and the magnetic end 1414 are positioned approximate to one another as separated by the tissue 1409.

In one embodiment, the control 1408 is connected to the second magnet 1406 and a power source or battery (not shown). The control 1408 may be configured to turn the second magnet 1406 on and off as well as control the intensity of the magnetic field generated by the second magnet 1406. In another embodiment, the positioner 1401 or second magnet 1406 may be configured to allow the second magnet 1406 to move about the periphery or between locations on the surface contact 1413 in order to position the wireless endoscope 1412 including the magnetic collar 1416 without rotating the positioner 1401. For example, the second magnet 1406 may be positioned in a carousel, on a rail, slidable fixture, or so forth. The positioner 1401 or second magnet 1406 may be configured to allow the second magnet 1406 to rotate to further adjust the orientation of the wireless endoscope 1412. The intensity of the magnetic field generated by the second magnet 1406 may also be controlled by shielding, partially shielding or completely shielding the second magnet 1406. For example, a shielding member or layer (not shown) may be slid, rotated or attached in a partial or full covering position over the second magnet 1406.

In one embodiment, the wireless endoscope 1412 may be attached or anchored to the positioner 1401 by the lanyard 1410. The lanyard 1410 may be a cable, wire, rope, string, or other connector that physically tethers, anchors or connects the positioner 1401 to the wireless endoscope 1412. The lanyard 1410 may be formed of a sterilized or medicated material (e.g., anti-bacterial, antibiotic, etc.) and include rounded edges that prevent abrasions, cuts, or other trauma to the opening 1411, the cavity 1413, or other portions of the patient's body.

The positioner 1401 and the wireless endoscope 1412 may include miniature hooks, latches, collars, clasps, rings, pins, or other securing components for attaching the lanyard 1410 between the positioner 1401 and the wireless endoscope 1412. In other embodiments, the lanyard 1410 may be physically connected to the patient, such as tied to an arm, taped to the abdomen, or so forth. The lanyard 1410 provides a safety mechanism and backup for retrieving the wireless endoscope 1412 should the positioner 1401 be unable to magnetically influence and secure the wireless endoscope 1412. Although not shown, the positioner 1401 may be utilized to secure and position any number of medical instruments, tools, or equipment. In one embodiment, inserted medical equipment, tools or inserts may include magnets for being maneuvered by the positioner 1401. The magnets may also be utilized for visualization by an external imaging system, such as an ultrasound, MRI, or x-ray. The magnets may also be utilized to position radiation delivery systems, scopes (e.g., laparoscopes, endoscopes, fiberoptic scopes, etc.), hypodermics, air-pressure injection systems, catheters, laser systems, robotics, or so forth. As a result, the positioner 1401 and wireless endoscope 1412 may include sensors (not shown) for magnetic, visual light, radio frequency sensing as well as any number of other particles, emissions, or standards.

As shown, the wireless endoscope 1412 may communicate directly or indirectly with the computing device 1422 utilizing the wireless signal 1421. The computing device 1422 may include an interface, such as a Bluetooth transceiver, WiFi transceiver, or RF transceiver for communicating with the wireless endoscope 1412, or may include an adapter, dongle, or externally connected peripheral for communication. In one embodiment, one or more of the wireless endoscope 1412, positioner 1401, and the computing device 1422 may utilize a processor, memory, application specific integrated certificate (ASIC), field programmable gate array (FPGA), or other logic to store and execute an application configured to control and manage content retrieved by the wireless endoscope 1412. In another embodiment, a default image viewing program, operating system, kernel, or media player may be utilized to view the content captured by the camera 1418 and communicated to the computing device 1422 through the wireless signal 1421.

Figure 15:
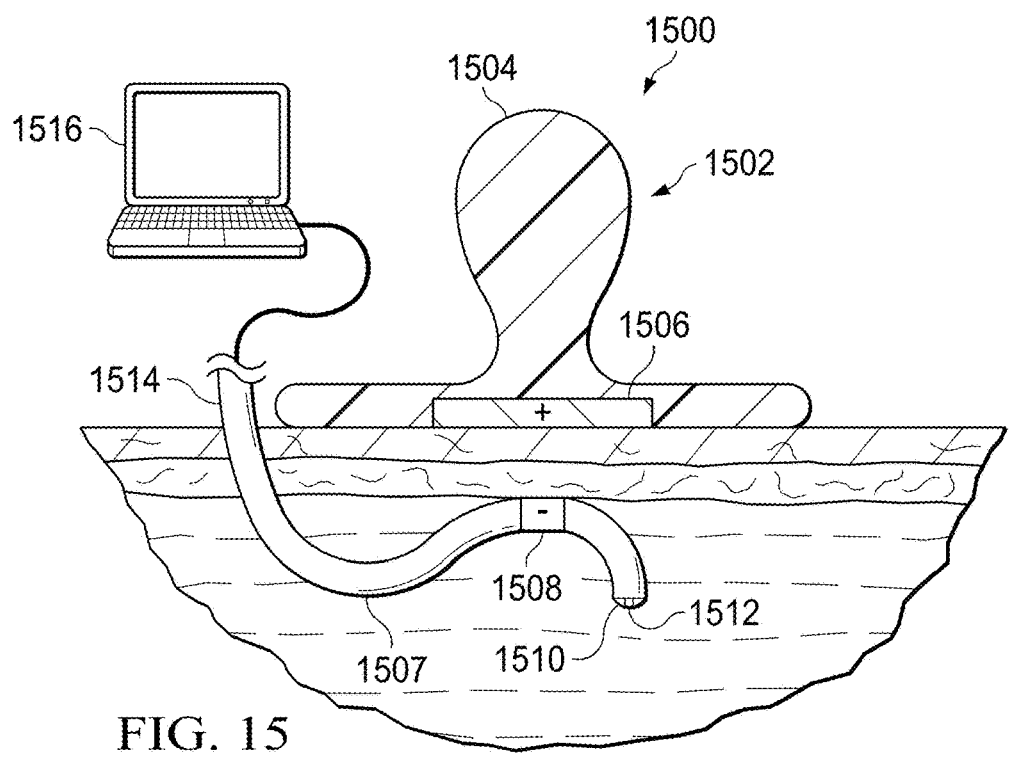
FIG. 15 is schematic, pictorial representation of another endoscopic system in accordance with an illustrative embodiment.

FIG. 15 is schematic, pictorial representation of another endoscopic system 1500 in accordance with an illustrative embodiment. In one embodiment, the endoscopic system 1500 may include a positioner 1502, a handle 1504, a first magnet 1506, a wired endoscope 1507, a second magnet 1508, a camera 1510, a light 1512, a cable 1514, and a computing device 1516. As shown and discussed in the previous embodiments, the handle 1504 may take various shapes.

In this embodiment, the handle 1504 has a door knob or bell shape for easy manipulation by the user. The handle 1504 also has an expanded surface area for easily rotating the positioner 1502 during use. The positioner 1502 includes one or more magnets, such as the first magnet 1506 for securing, orienting, positioning, and moving the wired endoscope 1507 and the corresponding second magnet 1508. In one embodiment, the wired endoscope 1507 may be configured to physically interface with an electronic device, such as the computing device 1516. The computing device 1516 is representative of any number of electronic devices as was previously described, and may be plug-and-play compatible requiring little or no custom software or hardware to interface with the wired endoscope 1507.

In one embodiment, the second magnet 1508 is integrated with the wired endoscope 1507. For example, a portion of the cable 1514 or head of the wired endoscope 1507 may be replaced or configured with a magnet to control movement and positioning of the associated camera 1510 and the light 1512. In one embodiment, the wired endoscope 1507 includes an internal structure and supports or outer body configured to hold a particular shape as implemented by the user bending the wired endoscope 1507. As a result, the wired endoscope 1507 may be configured and angled before being inserted into a body of a patient. In another embodiment, the wired endoscope 1507 may include cables, wires, actuators, pneumatics, motors, micro-electric machines (MEMs), memory materials or other mechanisms, components or devices for moving, orienting, positioning, and angling the wired endoscope 1507 when placed within the body. Existing wired endoscopes 1507 and components for positioning the wired endoscope 1507 are known in the art.

The cable 1514 may be sterilized for substantial insertion into the body of the patient. For example, the overall wired endoscope 1507 may be prepackaged or sterilized prior to performing the medical procedure. In one embodiment, once the first magnet 1506 and second magnet 1508 are secured, the cable may be utilized to orient (e.g., change the position or angle of) the camera 1510. For example, excess cable 1514 may be inserted into the body of the patient while the positioner 1502 is held still in order to rotate the camera 1510 generally about an axis passing through the first magnet 1506 and second magnet 1508.

In another embodiment, both the positioner 1502 and the wired endoscope 1507 may include one or more additional magnets that allow the positioner 1502 to better control the position and orientation of the wired endoscope 1507. In another embodiment, the second magnet 1508 is attached to the wired endoscope 1507. For example, the second magnet 1508 may be a magnetic collar that is slid into position on the wired endoscope 1507. In another embodiment, the second magnet 1508 is configured to be clamped onto the wired endoscope 1507 at a specified position that may aid in orienting the wired endoscope 1507 to be conducive to viewing or facilitating the medical procedure. The second magnet 1508 may utilize any number of securing mechanisms or components, such as adhesives, buckles, clamps, rings, belts, and sleeves. As with other embodiments, the positioner 1502 or first magnet 1506 may be configured to allow the first magnet 1506 to be repositioned or reoriented to further control the orientation of the wired endoscope 1507.

Figure 16:
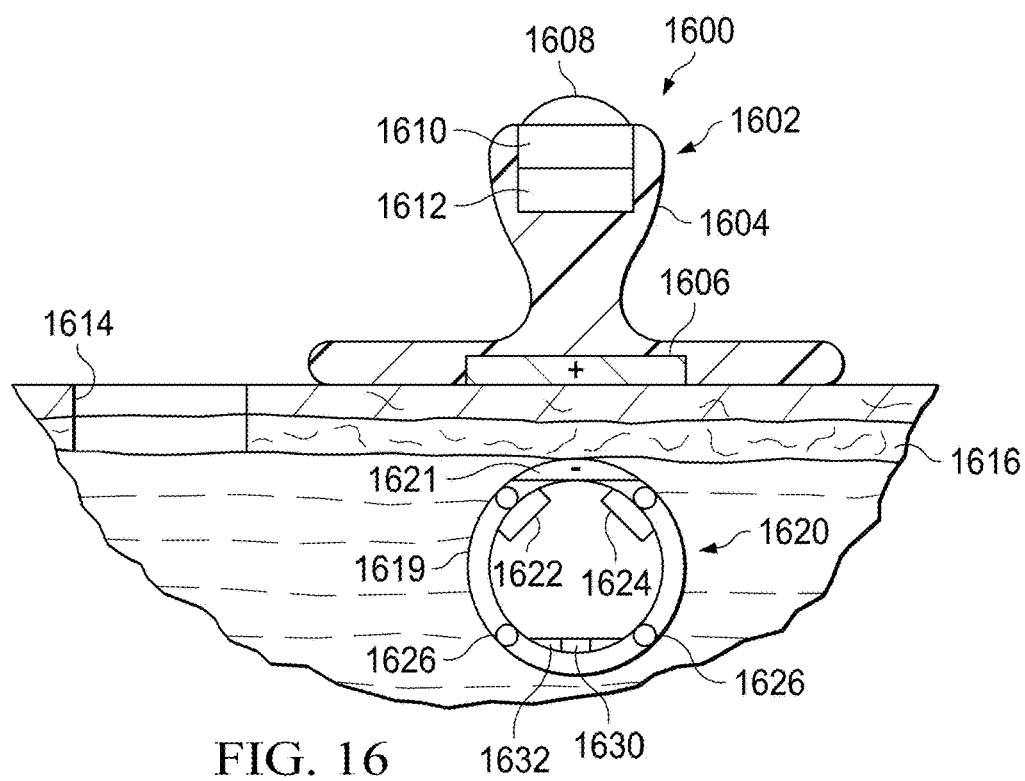
FIG. 16 is a schematic, side view of another endoscopic system in accordance with an illustrative embodiment.

FIG. 16 is a schematic, side view of another endoscopic system 1600 in accordance with an illustrative embodiment. In one embodiment, the endoscopic system 1600 may include a positioner 1602, a handle 1604, a first magnet 1606, a directional controller 1608, logic 1610, and a transceiver 1612. A magnetic endoscope 1620 may be inserted through an opening 1614 in tissue 1616. In one embodiment, the magnetic endoscope 1620 may include a second magnet 1621, a first drive motor 1622, a second drive motor 1624, bearings 1626, a camera 1630, and a light 1632.

The endoscopic system 1600 may utilize a round shaped magnetic endoscope 1620 to prevent internal injuries or damage to the patient. The round shape of the magnetic endoscope 1620 may also facilitate the smooth movement, rolling, or positioning of the magnetic endoscope 1620 within the body of the patient. As previously described, the first magnet 1606 may be attracted to the second magnet 1621 to control the relative proximity of the magnetic endoscope 1620 and the positioner 1602 during utilization. In one embodiment, the second magnet 1621 may be integrated with or connected to a case 1619 of the magnetic endoscope 1620. For example, all or a portion of the case 1619 may be magnetic or metallic for attraction to the first magnet 1606. In another embodiment, the case may include a number of magnets symmetrically or asymmetrically positioned around the periphery of the case 1619 for positioning the magnetic endoscope 1620 to visualize or view a particular area within the body of the patient.

In one embodiment, the positioner 1602 may be configured to wirelessly communicate with the magnetic endoscope 1620. As previously described, the magnetic endoscope 1620 may communicate with one or more electronic devices such as computing, communications, or medical devices. In another embodiment, the images and content captured by the camera 1630 may be streamed to the positioner 1602. The logic 1610 may include a processor, memory, digital logic, applications, or instructions for communicating with and controlling the magnetic endoscope 1620. In another embodiment, the positioner 1602 may be connected to or integrated with a display that may display the content from the magnetic endoscope 1620 as processed and received by the positioner 1602 and attached display. The magnetic endoscope 1620 may include any of the hardware, software, features, and other components as have previously been described.

In one embodiment, the directional controller 1608 is a track ball. In another embodiment the directional controller 1608 may be a toggle, button or multiple buttons, optical scanner for the user's thumb or hand or other interface components for controlling the motion and position of the magnetic endoscope 1620 as are known in the art. In one embodiment, the handle 1604 or directional controller 1608 may make up a moveable joy stick that may be utilized to position the magnetic endoscope 1620 based on motion performed by the user. The motion of the directional controller 1608 is translated by the logic 1610 into commands and other signals that are sent by the transceiver 1612 to a transceiver, logic, and motor control (not shown) of the magnetic endoscope 1620. In another embodiment, the directional controller 1608 may include buttons, scroll wheels, or other control mechanisms for digitally or controlling the motion and positioning of the magnetic endoscope 1620. Other linked devices, such as wireless devices, tablets, computers, laptops, motion sensing systems, actuators, virtual reality systems, electronic glasses, or so forth may be utilized to control motion, positioning, and functionality of the magnetic endoscope 1620.

In other embodiments, the magnetic endoscope 1620 may be swallowed, injected, inserted, or so forth within the body while still being manipulated, moved, positioned, controlled, or powered by the handle 1604 or other linked devices. For example, the magnetic endoscope 1620 may be miniature to fit within intestines, cavities, veins, or so forth. In addition, a close proximity between the handle 160 and the magnetic endoscope 1620 may not be required to operate the endoscopic system 1600. For example, the camera 1630 may be rotated and controlled utilizing the handle 1604 or a separate wireless device, such as a cell phone. Power may be wirelessly communicated (electromagnetic induction, inductive coupling, microwave transmissions, electrodynamic induction, resonant inductive coupling, etc.) to the magnetic endoscope 1620 that may include a receiver or inductor for processing the received power or magnetic signal for capturing and utilizing the power for long-term operation of the magnetic endoscope 1620.

The magnetic endoscope 1620 may include any number of drive or control motors as are shown to drive the motion of internal components, such as the camera 1630 and light 1632. For example, the internal components may be positioned in contact with the first drive motor 1622, the second drive motor 1624 and the bearings 1626 to allow the internal components to be freely moved or positioned within the magnetic endoscope 1620. In one embodiment, the first drive motor 1622 may drive the internal components in a first direction, such as an X axis or X direction and the second motor 1624 may drive the internal components in a second direction, such as a Y axis or Y direction. As a result, utilizing these two or more motors, the camera 1630 may be positioned in any direction or angle that may be required to view an internal portion of the body of the patient. For example, the motion of the directional controller 1608 may directly correlate to the motion of the internal components including the camera 1630 allowing the user to envision and position the camera 1630 in a way that is intuitive based on the motion of the directional controller 1608. As previously described, any one of the drives, controls, motors or other actuators controlling motion of internal components of the magnetic endoscope 1620 (e.g., camera 1630, light 1632, second magnet 1621, etc.) may be powered wirelessly, for example, by the positioner 1600. In another embodiment, the direction and motion of one or more of the internal components of the magnetic endoscope 1620, such as camera 1630, light 1632, second magnet 1621, etc., may be controlled utilizing one or more material types that have properties that can be significantly changed in a controlled fashion by a stimuli such as stress, temperature, moisture, pH, electric or magnetic fields. For example, one or more smart materials may be employed to control the movement and position of any one of the aforementioned components of the magnetic endoscope 1620. For example, piezoelectric materials that bend, expand or contract when a voltage is applied may be used. Shape-memory alloys and shape-memory polymers that undergo deformation that is induced and recovered through temperature changes or stress may also be utilized. One or more magnetostrictive materials that exhibit change and shape under the influence of a magnetic field or flux may also be employed. A magnetic shape memory alloy that changes its shape in response to a magnetic field may be utilized. Other materials that may be utilized to control movement and direction of the internal components or one or more external components include pH-sensitive polymers that change in volume when the pH of the surrounding medium changes, responsive polymers which undergo deformation upon change in temperature, photo mechanical materials that change shape under exposure to light, and dielectric elastomers (DES) that deform under the influence of an external electric field.

In another embodiment, instead of motors, the internal components may be configured to slidably move within the case 1619 as a result of one or more slippery surfaces, lubrications, or so forth. For example, a number of other magnets of the positioner 1602 and the internal components may be configured to allow the user to angle and position the internal components including the camera 1630. For example, an electromagnet placed at an edge, surface or periphery of the positioner 1602 may be increased or decreased in strength to rotate the internal components or the camera 1630. As described, the bearings 1626 allow the internal components to move or rotate smoothly within the case 1619. The internal components may move or translate based on the performed motion or drive of the first drive motor 1622 and the second drive motor 1624. The internal components may be biased in one direction or another, for example by a spring or other resistive member, until acted upon magnetically or mechanically.

Figure 17:
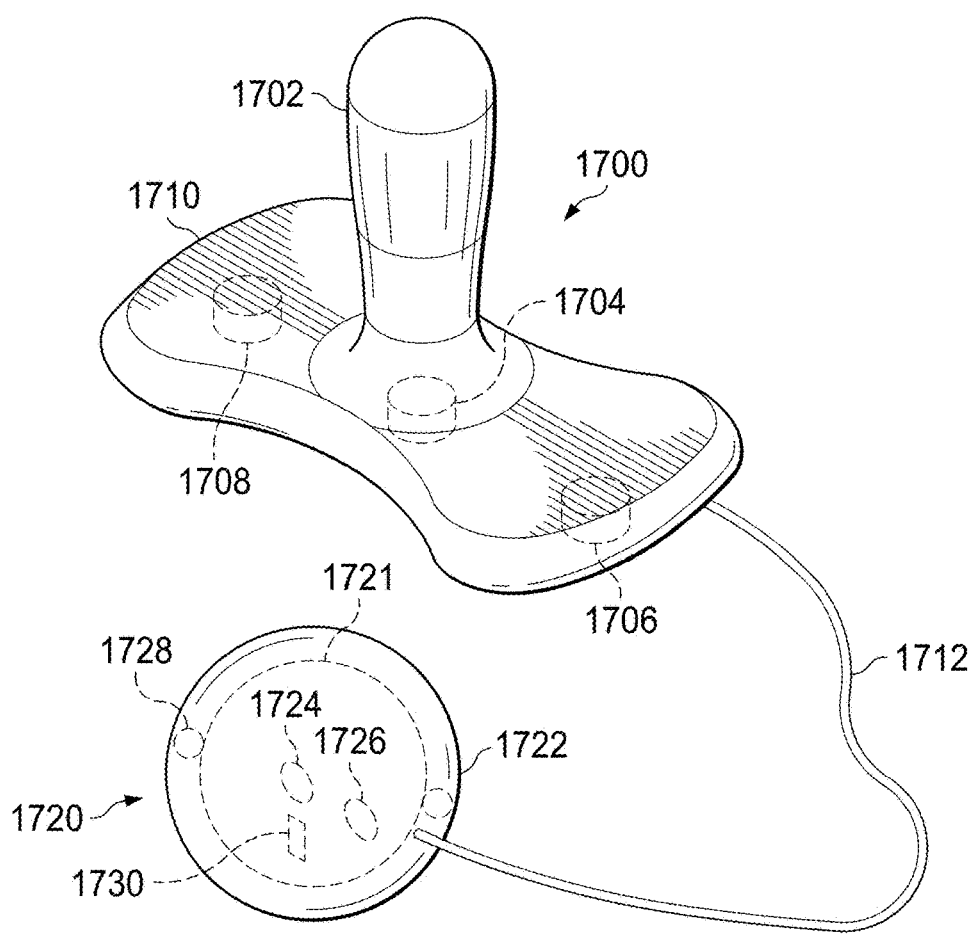
FIG. 17 is a schematic, pictorial representation of a positioner and a wireless endoscope in accordance with illustrative embodiment.

FIG. 17 is a schematic, pictorial representation of a positioner 1700 and a wireless endoscope 1720 in accordance with an illustrative embodiment. In one embodiment, the wireless endoscope 1720 may be spherically shaped. However, any number of sizes and shapes may be utilized without limitation. For example, the wireless endoscope 1720 may be cylindrically shaped (as shown in FIG. 17), pill shaped, oblong, elliptical, fiber shaped, disk shaped, or asymmetrical based on the different applications.

In one embodiment, the positioner 1700 may include a handle 1702, a first magnet 1704, a second magnet 1706, a third magnet 1708, and a base 1710. The positioner 1700 may be connected to the wireless endoscope 1720 by a lanyard 1712. The wireless endoscope 1720 may include a magnetic case 1722, a camera 1724, a magnet 1726, light 1730, and bearings 1728.

In one embodiment, the positioner 1700 may have an hourglass or dog bone shape with the base which may include a flat bottom for being moved against the patient's skin or tissue. The handle 1702 may have a narrower shaft and a wider top for moving the positioner 1700 and gripping the top of the handle 1702 when rotating the positioner 1700.

The second magnet 1706 and the third magnet 1708 may be configured to be moved along an end or edge of the base 1710. For example, the base 1710 may define a slit, opening, pocket, slidable fixture, track, or rail for moving the second magnet 1706 and the third magnet 1708. The second magnet 1706 and the third magnet 1708 may be configured to be moved, slid, translated, or configured by the user or automatically in response to commands received through electrical, mechanical or other control components of the positioner 1700. As previously described, the first magnet 1704, the second magnet 1706, and the third magnet 1708 may be naturally occurring, man-made, or electro magnets. In other embodiments, the described magnets may be configured to be perpendicularly adjusted away from the bottom of the base 1710 or toward the bottom of the base 1710. The magnets may be moved in any x, y, or z direction as secured by the positioner 1700. For example, the magnets may be oriented relative to the bottom of the base 1710 to further control the orientation and movement of the wireless endoscope 1720.

In one embodiment, the first magnet 1704 may be configured to attract the magnetic case 1722. The internal electrical components 1721 of the wireless endoscope 1720 may include an additional magnet 1726 or magnets for rotating the electrical components 1721 within the magnetic case 1722. For example, the magnet 1726 may be attracted to the second magnet 1706 or the third magnet 1708 to move and position the electrical components 1721 including the camera 1724.

The electrical components 1721 may be configured to move, rotate, or pivot within the magnetic case 1722 based on the separation of the electrical components 1721 from the magnetic case 1722 by the bearings 1728. The bearings 1728 allows the electrical components to move as controlled by the magnet 1726, motors, or other locomotion components (not shown). The bearings 1728 may be integrated with the magnetic case 1722 or electrical components 1721 to allow the electrical components 1721 to rotate within the magnetic case 1722. For example, the bearings 1728 may be positioned at equal distances throughout the magnetic case 1722 to allow the necessary rotation.

Figure 18:
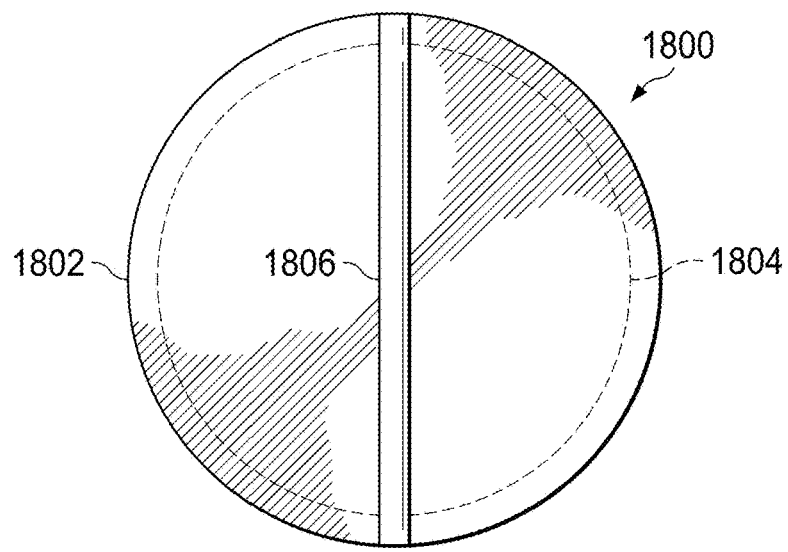
FIG. 18 is a schematic, pictorial representation of a wireless endoscope in accordance with illustrative embodiment.

FIG. 18 is a schematic, pictorial representation of a wireless endoscope 1800 in accordance with illustrative embodiment. In one embodiment, the wireless endoscope 1800 may include a case 1802, electrical components 1804, and a conductor 1806.

In one embodiment, the wireless endoscope 1800 may have a clear or transparent case 1802 with a conductor 1806 extending narrowly around the circumference of the case 1802. For example, the conductor 1806 may represent a magnetic conductor, such as steel, or a circular magnet integrated with or connected to the case 1802. The circular conductor 1806 may allow the wireless endoscope 1800 to be rolled into position around, over, or through internal obstacles within the body of the patient. The wireless endoscope 1800 may be moved perpendicular to a plane of the conductor 1806 so that the conductor 1806 does not block a view of a camera of the wireless endoscope 1800 (not shown).

The previous detailed description is of a small number of embodiments for implementing the invention and is not intended to be limiting in scope. The following claims set forth a number of the embodiments of the invention disclosed with greater particularity.

What is claimed:

1. An endoscopic system, comprising:
   a plurality of magnets of varying magnetic strength;
   a wireless endoscope configured to be inserted into a body of a patient, the wireless endoscope comprising:
   (a) one or more magnets selected from the plurality of magnets based on magnetic strength;
   (b) a sensor; and
   (c) a light source;
   a positioner comprising:
   (a) at least one magnet selected from the plurality of magnets based on magnetic strength and the selected magnet for the wireless endoscope for attracting the one or more magnets and configured for magnetically moving the wireless endoscope within the body of the patient;
   b) a handle portion comprising having distal and proximal ends, the handle portion having generally parallel opposing circumferential surfaces in longitudinal cross section;
   (c) a flanged surface connected to and extending generally perpendicularly and radially outwardly from the circumferential surface of the handle portion to a terminal edge, the flanged surface having a bottom configured to externally contact the body of the patient, wherein the handle portion extends orthogonal to the flanged surface, and wherein the at least one magnet is contained within the flanged surface; and
   (d) a directional controller on the proximal end of the handle portion and extending outside the handle portion for user-controlled motion and movement of the wireless endoscope, wherein the at least one magnet has an on/off and a magnetic field intensity controlled by the directional controller wherein the at least one magnet is movable about one or more positions on the flanged surface to control the magnet field intensity.

2. The endoscopic system of claim 1 wherein the light source has an emittance and the sensor has a collector for acquiring a reflection response from within the body of the patient.

3. The endoscopic system of claim 1 wherein the sensor comprises a camera and the light source comprises a light.

4. The endoscopic system of claim 3 further comprising:
   a display in communication with the endoscope for displaying imagery captured by the camera.

5. The endoscopic system of claim 1, wherein both the endoscope and the positioner include at least two magnets for magnetically (1) moving the endoscope and (2) angling the sensor and the light source.

6. The endoscopic system of claim 1 wherein the positioner further comprises:
   (a) a wireless transceiver; and
   (b) a processor,
   wherein the wireless transceiver and the processor are disposed within the handle portion of the positioner.

7. The endoscopic system of claim 1 further comprising:
   a first magnet disposed proximate the flanged surface beneath the handle portion, the first magnet of the positioner for attracting one of the one or more magnets in the wireless endoscope; and
   a second magnet disposed proximate the flanged surface adjacent the terminal edge of the flanged surface for attracting another one of the one or more magnet in the wireless endoscope.

* * * * *